(12) United States Patent
Manicke et al.

(10) Patent No.: US 11,998,907 B2
(45) Date of Patent: Jun. 4, 2024

(54) CARTRIDGES, SYSTEMS AND METHODS FOR MASS SPECTROMETRY

(71) Applicant: The Trustees of Indiana University, Bloomington, IN (US)

(72) Inventors: Nicholas Edward Manicke, Zionsville, IN (US); Chengsen Zhang, Indianapolis, IN (US)

(73) Assignee: The Trustees of Indiana University, Bloomington, IN (US)

( * ) Notice: Subject to any disclaimer, the term of this patent is extended or adjusted under 35 U.S.C. 154(b) by 883 days.

(21) Appl. No.: 17/046,573

(22) PCT Filed: Apr. 11, 2019

(86) PCT No.: PCT/US2019/027082
§ 371 (c)(1),
(2) Date: Oct. 9, 2020

(87) PCT Pub. No.: WO2019/200166
PCT Pub. Date: Oct. 17, 2019

(65) Prior Publication Data
US 2021/0387175 A1     Dec. 16, 2021

Related U.S. Application Data

(60) Provisional application No. 62/656,306, filed on Apr. 11, 2018.

(51) Int. Cl.
*B01L 3/00* (2006.01)
*G01N 33/68* (2006.01)

(52) U.S. Cl.
CPC .......... *B01L 3/502* (2013.01); *G01N 33/6848* (2013.01); *B01L 2200/025* (2013.01);
(Continued)

(58) Field of Classification Search
None
See application file for complete search history.

(56) References Cited

U.S. PATENT DOCUMENTS 7,070,682 B2 * 7/2006 Lee ................. G01N 27/44791
204/462
2002/0015667 A1   2/2002 Chow
(Continued)

FOREIGN PATENT DOCUMENTS

JP    2017/096727    6/2017
WO   2016130646 A1   8/2016

OTHER PUBLICATIONS

Narayanan, R. et al. Molecular Ionization from Carbon Nanotube Paper, Angew. Chem. Int. Ed. 2014, 53, 5936-5940. (Year: 2014).*
(Continued)

*Primary Examiner* — Xiaoyun R Xu
(74) *Attorney, Agent, or Firm* — Barnes & Thornburg LLP

(57) ABSTRACT

The present disclosure provides "all-in-one" cartridges which contain necessary reagents and materials to isolate/preconcentrate targeted proteins from blood plasma and ionize them for mass spectrometry detection. In another configuration, the cartridges include proteolytic enzymes to digest the proteins into smaller peptides in addition to preconcentration and ionization for mass spectrometry detection.

20 Claims, 32 Drawing Sheets

(52) U.S. Cl.
CPC ... *B01L 2200/16* (2013.01); *B01L 2300/0609* (2013.01); *B01L 2300/069* (2013.01); *B01L 2300/12* (2013.01); *B01L 2400/027* (2013.01)

(56) References Cited

U.S. PATENT DOCUMENTS

| | | |
|---|---|---|
| 2004/0166031 A1 | 8/2004 | Taylor |
| 2006/0257991 A1 | 11/2006 | McDevitt |
| 2016/0169892 A1* | 6/2016 | Ke .................. C07K 16/40 530/391.1 |
| 2016/0214031 A1 | 7/2016 | Blaschyk |
| 2017/0082604 A1* | 3/2017 | Ouyang ........... G01N 33/48714 |

OTHER PUBLICATIONS

Zhang, Chengsen et al., "Targeted Protein Detection Using an All-in-One Mass Spectrometry Cartridge", Journal of the American Chemical Society, 2017, 139, pp. 10996-10999.

Pu, Fan et al., "Direct sampling mass spectrometry for clinical analysis", Royal Society of Chemistry, Analyst, 2019, 144, pp. 1034-1051.

Supplementary European Search Report, issued by the European Patent Office, dated Nov. 5, 2021, for European Application No. EP19785590; 7 pages.

International Search Report and Written Opinion issued by the International Searching Authority, dated Jul. 8, 2019, for International Patent Application No. PCT/US2019/27082; 7 pages.

Pu et al., "Direct sampling mass spectrometry for clinical analysis", Analyst, vol. 144, No. 4, Dec. 3, 2018, pp. 1034-1051.

Zhang et al., "Targeted Protein Detection Using an All-in-One Mass Spectrometry Cartridge", Journal of The American Chemical Society, vol. 139, No. 32, 2017, pp. 10996-10999.

* cited by examiner

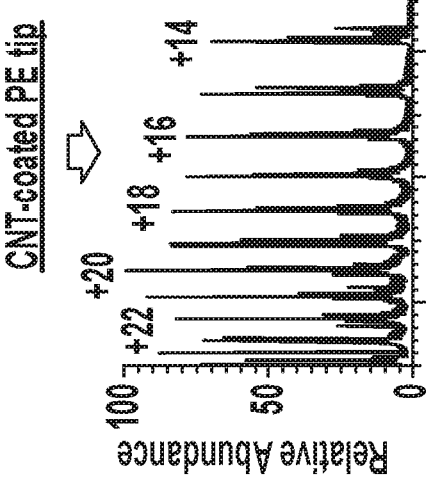
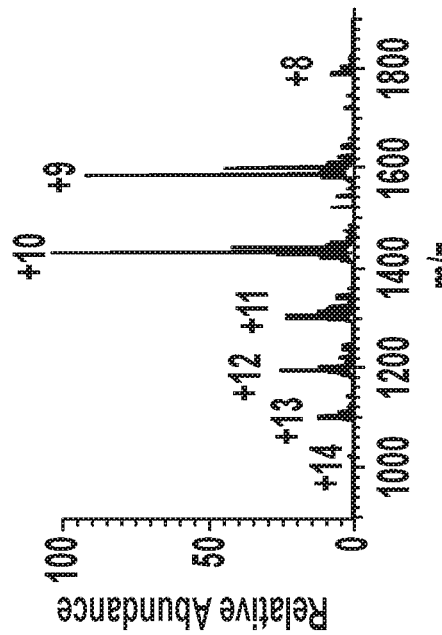
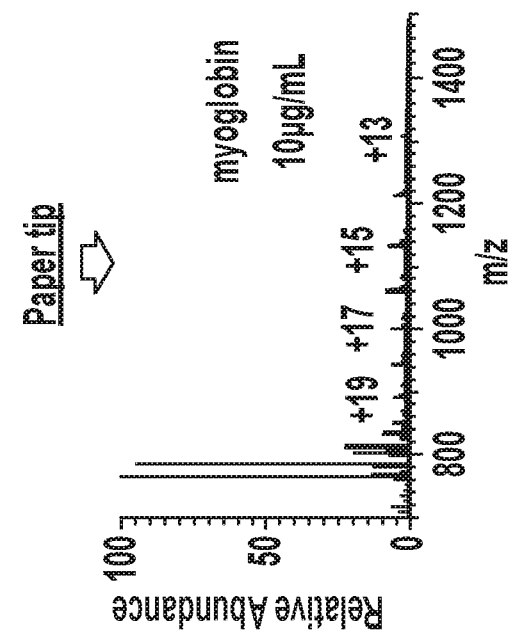
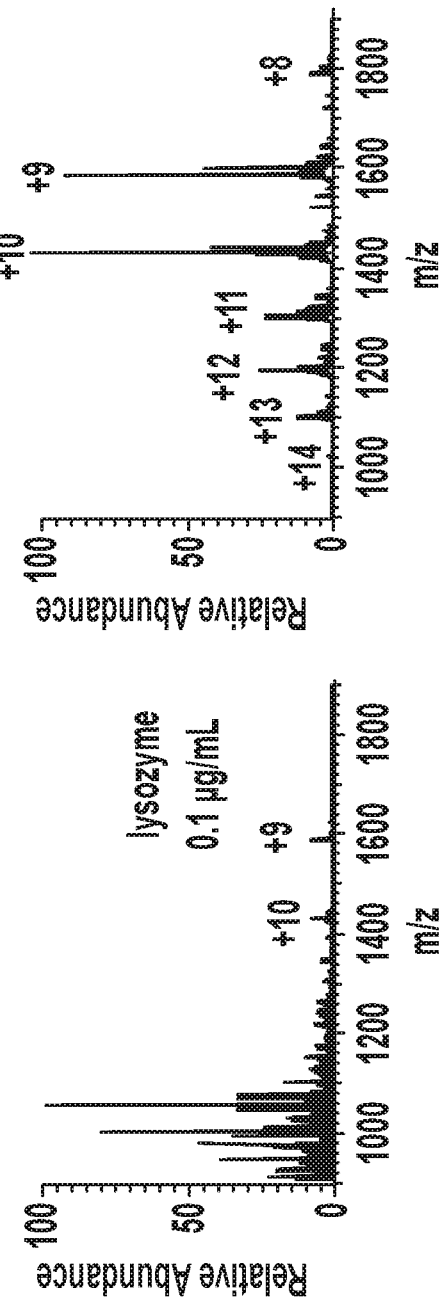
FIG. 18A
FIG. 18B
FIG. 18C
FIG. 18D

CARTRIDGES, SYSTEMS AND METHODS FOR MASS SPECTROMETRY

CROSS-REFERENCE TO RELATED APPLICATIONS

This application is a national stage entry of International (PCT) Patent Application Number PCT/US2019/027082, filed on Apr. 11, 2019, which in turn claims the benefit of and priority to U.S. Provisional Application Ser. No. 62/656,306, filed on Apr. 11, 2018, the entire disclosures of which are hereby expressly incorporated by reference in their entirety.

FIELD OF THE DISCLOSURE

The present disclosure relates generally to an apparatus for use with mass spectrometry and more particularly, a cartridge apparatus for use with mass spectrometry.

BACKGROUND

Protein molecules are measured in clinical diagnostic laboratories as tumor markers, acute or chronic disease markers, risk or prognostic markers, and hormones. Immunoassays have been successfully used for decades to detect protein analytes in clinical laboratories, but there remain limitations of this approach. Monoclonal antibodies are expensive to develop and manufacture. Moreover, there are well recognized analytical limitations; for example, most immunoassays do not distinguish between the various proteoforms and variants of a protein present in clinical samples.

Targeted enrichment of proteins followed by mass spectrometry (MS) detection is a widely used approach to detect different proteoforms. Enrichment is generally performed using antibodies because of their ability to selectively enrich target proteins from protein rich matrices such as plasma. Mass spectrometric immunoassay (MSIA) uses antibody coated beads packed into a pipet tip followed by detection of intact proteins by MALDI-MS. Another approach is antibody modification of the MALDI target protein. In SIS-CAPA (stable isotope standards and capture by antipeptide antibodies) and immuno-MALDI, enrichment is performed at the peptide level after digestion. Peptide level enrichment gives better quantitation and improved sensitivity for detection. However, limited sequence coverage complicates detection of post translational modifications (PTMs) and sequence variants.

Improvements in the foregoing are desired.

SUMMARY OF THE DISCLOSURE

The present disclosure provides "all-in-one" cartridges which contain necessary reagents and materials to isolate/preconcentrate targeted proteins from blood plasma and ionize them for mass spectrometry detection. In another configuration, the cartridges include proteolytic enzymes to digest the proteins into smaller peptides in addition to preconcentration and ionization for mass spectrometry detection.

According to an embodiment of the present disclosure, a protein detection cartridge is provided. The protein detection cartridge comprises: a lid including an opening; a base coupled to the lid and including a recess; a column holder removably positioned in the opening, the column holder including an aperture configured to receive an antibody column; a waste pad removably positioned below the column holder and in the recess of the base; a holder removably positioned in the base, the holder including a recess; and an enzyme immobilized membrane positioned in the recess of the holder.

In another embodiment, wherein the column holder is movable between a first position where the antibody column is positioned over the waste pad and a second position where the antibody column is in contact with the enzyme immobilized membrane and positioned over a spray tip. In another embodiment, the column holder is movable between the first position and the second position along a groove between the lid and the base. In another embodiment, the antibody column includes an antibody coated membrane configured to retain target proteins. In another embodiment, the spray tip is configured to provide a sample to a mass spectrometer, the spray tip is coated with carbon nanotube treated porous polyethylene. In another embodiment, the cartridge is coupled an electrical power source.

In one particular embodiment, a protein detection cartridge is provided. The protein detection cartridge includes a lid including an opening; a base coupled to the lid and including a recess; a column holder removably positioned in the opening, the column holder including an aperture configured to receive an antibody column; a waste pad removably positioned below the column holder, the waste pad removably positioned in the recess of the base; a holder removably positioned in the base, the holder including a recess; an enzyme immobilized membrane positioned in the recess of the holder; and a spray substrate coupled to the holder; wherein the column holder is slidable within the cartridge between a first position and a second position; and wherein in the first position, the antibody column is above the waste pad and in the second position, the antibody column is in contact with the enzyme immobilized membrane and positioned over the spray substrate.

In another embodiment, the spray substrate is coated with carbon nanotube treated porous polyethylene. In another embodiment, the antibody column includes an antibody coated membrane to retain target proteins of a sample when the antibody column is in the first position. In another embodiment, the antibody column is above the enzyme immobilized membrane in the second position and the enzyme immobilized membrane digests the proteins into peptides. In another embodiment, the column holder is movable between the first position and the second position along a groove between the lid and the base. In another embodiment, the spray substrate is coupled to a mass spectrometer. In another embodiment, the cartridge is coupled an electrical power source.

In another embodiment, a method of using a protein detection cartridge for mass spectrometry is provided. The method of using a protein detection cartridge for mass spectrometry includes: setting a column holder of the protein detection cartridge in a first position, wherein the column holder includes an aperture configured to receive an antibody column; inserting a plasma sample into the antibody column of the protein detection cartridge, the plasma sample comprising proteins; inserting a wash buffer into the antibody column; sliding the column holder to a second position, wherein the antibody column is above an enzyme immobilized membrane of the protein detection cartridge; and inserting an elution buffer into the antibody column, wherein the proteins are digested to form a peptide via the enzyme immobilized membrane.

In another embodiment, the antibody column includes an antibody coated membrane to retain target proteins of a sample when the antibody column is in the first position. In another embodiment, the method further includes applying the peptide onto a spray substrate. In another embodiment, the spray substrate is coated with carbon nanotube treated porous polyethylene. In another embodiment, the spray substrate is coupled to a mass spectrometer. In another embodiment, the cartridge is coupled to an electrical power source.

Additional features and advantages of the present disclosure will become apparent to those skilled in the art upon consideration of the following detailed description of the illustrative embodiment exemplifying the best mode of carrying out the disclosure as presently perceived.

BRIEF DESCRIPTION OF THE DRAWINGS

The foregoing aspects and many of the intended advantages of this disclosure will become more readily appreciated as the same becomes better understood by reference to the following detailed description when taken in conjunction with the accompanying drawings, wherein:

FIG. 18 shows full mass spectra data obtained by ionizing 10 μg/mL myoglobin and 0.1 μg/mL lysozyme using paper spray (a,c) and the CNT-coated PE substrate (b,d);

Figure 1:
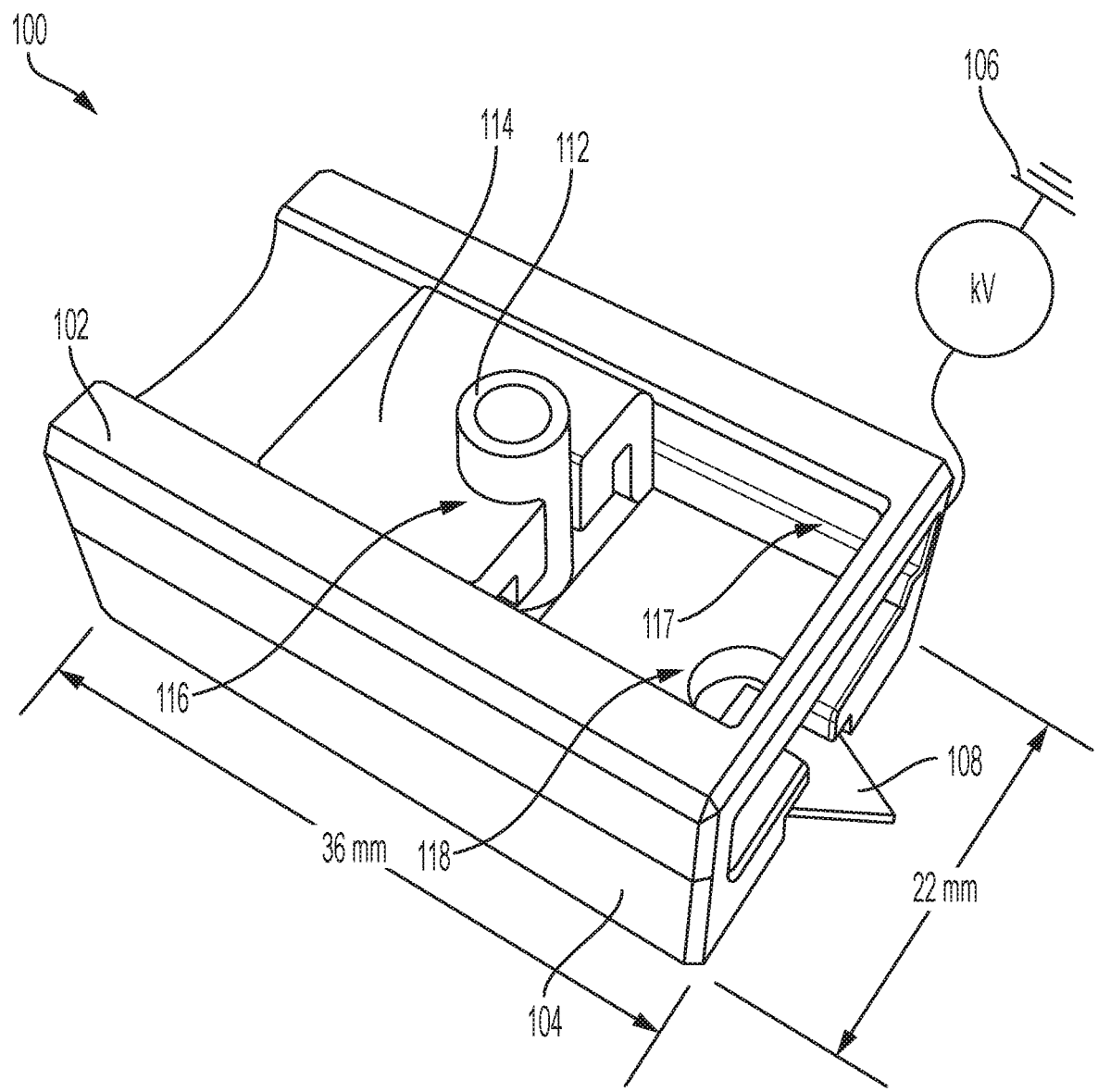
FIG. 1 is a perspective view of a cartridge used for intact protein analysis in accordance with the present disclosure.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplifications set out herein illustrate embodiments of the disclosure, and such exemplifications are not to be construed as limiting the scope of the disclosure in any manner.

DETAILED DESCRIPTION OF THE DRAWINGS

For the purposes of promoting an understanding of the principles of the disclosure, reference will now be made to the embodiments illustrated in the drawings, which are described below. The embodiments disclosed below are not intended to be exhaustive or limit the disclosure to the precise form disclosed in the following detailed description. Rather, the embodiments are chosen and described so that others skilled in the art may utilize their teachings. It will be understood that no limitation of the scope of the disclosure is thereby intended. The disclosure includes any alterations and further modifications in the illustrative devices and described methods and further applications of the principles of the disclosure which would normally occur to one skilled in the art to which the disclosure relates.

The present disclosure provides "all-in-one" cartridges which contain necessary reagents and materials to isolate/preconcentrate targeted proteins from blood plasma and ionize them for mass spectrometry detection. In another configuration, the cartridges include proteolytic enzymes to digest the proteins into smaller peptides in addition to preconcentration and ionization for mass spectrometry detection.

Figure 2:
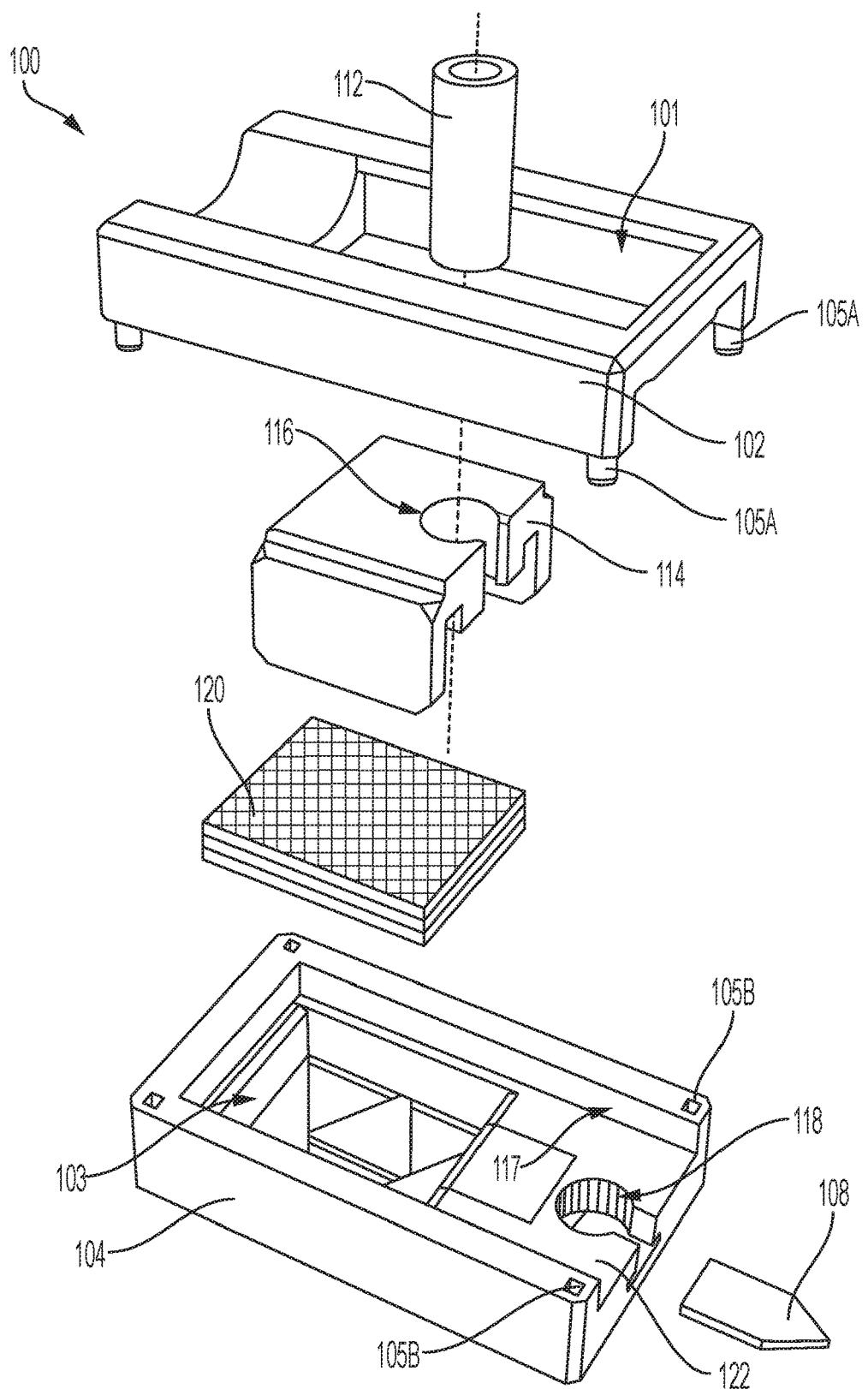
FIG. 2 is an exploded view of the cartridge of FIG. 1.

Referring to FIGS. 1 and 2, a cartridge 100 is shown. Cartridge 100 can be coupled to an electrical power source 106 (e.g., high voltage power supply), and cartridge 100 is generally used for intact protein analysis. However, it is contemplated that cartridge 100 can be used for other methods of protein analysis (e.g., protein digestion). Cartridge 100 includes a lid 102 coupled to base 104. As shown in FIG. 2, lid 102 includes tabs 105A that are received in recesses 105B to couple lid 102 to base 104. It is contemplated that other coupling means may be used to couple lid 102 to base 104. Lid 102 includes an opening 101 configured to receive a column holder 114 and a spray tip holder 122. Column holder 114 is removably positioned in opening 101 and includes a substantially circular aperture 116 configured to receive an antibody column 112, which comprises of a plastic tube packed with glass fiber membranes coated with latex bead-antibody conjugates. Column holder 114 also holds an absorbent waste pad 120 beneath aperture 116. That is, absorbent waste pad 120 is removably positioned in base 104. Further, absorbent waste pad 120 functions to draw the sample through antibody column 112.

All parts of cartridge 100 are assembled together, and column holder 114 slides along groove 117 between lid 102 and base 104 to switch the position of antibody column 112 from above waste pad 120, where the sample addition and washing steps occur, to above the spray substrate 108 where ionization by substrate supported electrospray ionization occurs.

Base 104 includes a recess 103 configured to receive column holder 114 and absorbent waste pad 120. Base 104 also includes holder 122 integrally formed with base 104. Holder 122 is configured to couple to a spray tip or spray substrate 108 where spray tip 108 functions to spray a sample to a mass spectrometer 300 (FIG. 5) as described in further detail herein.

Figure 3:
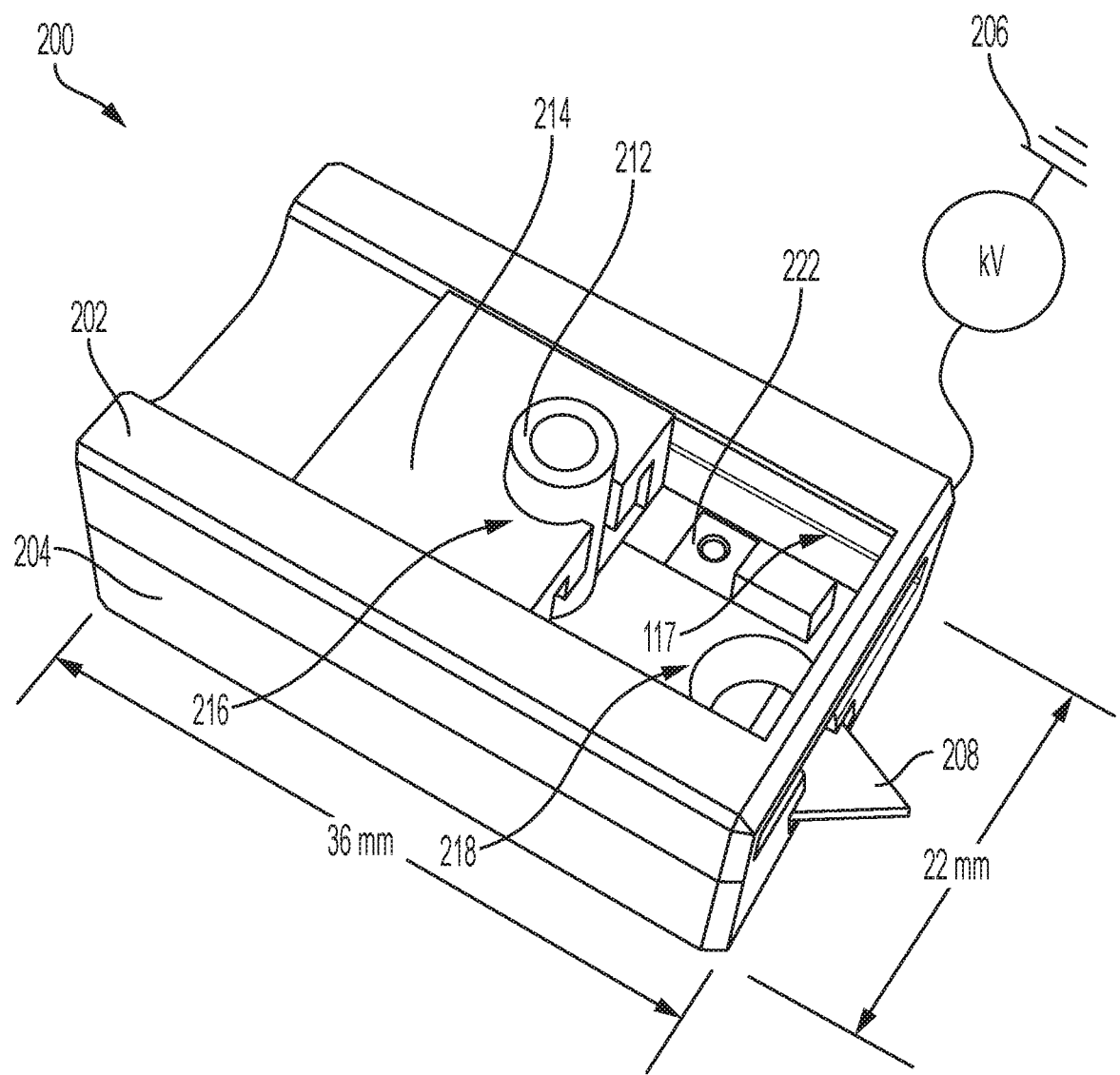
FIG. 3 is a perspective view of a cartridge used for protein digestion analysis in accordance with the present disclosure.
Figure 4:
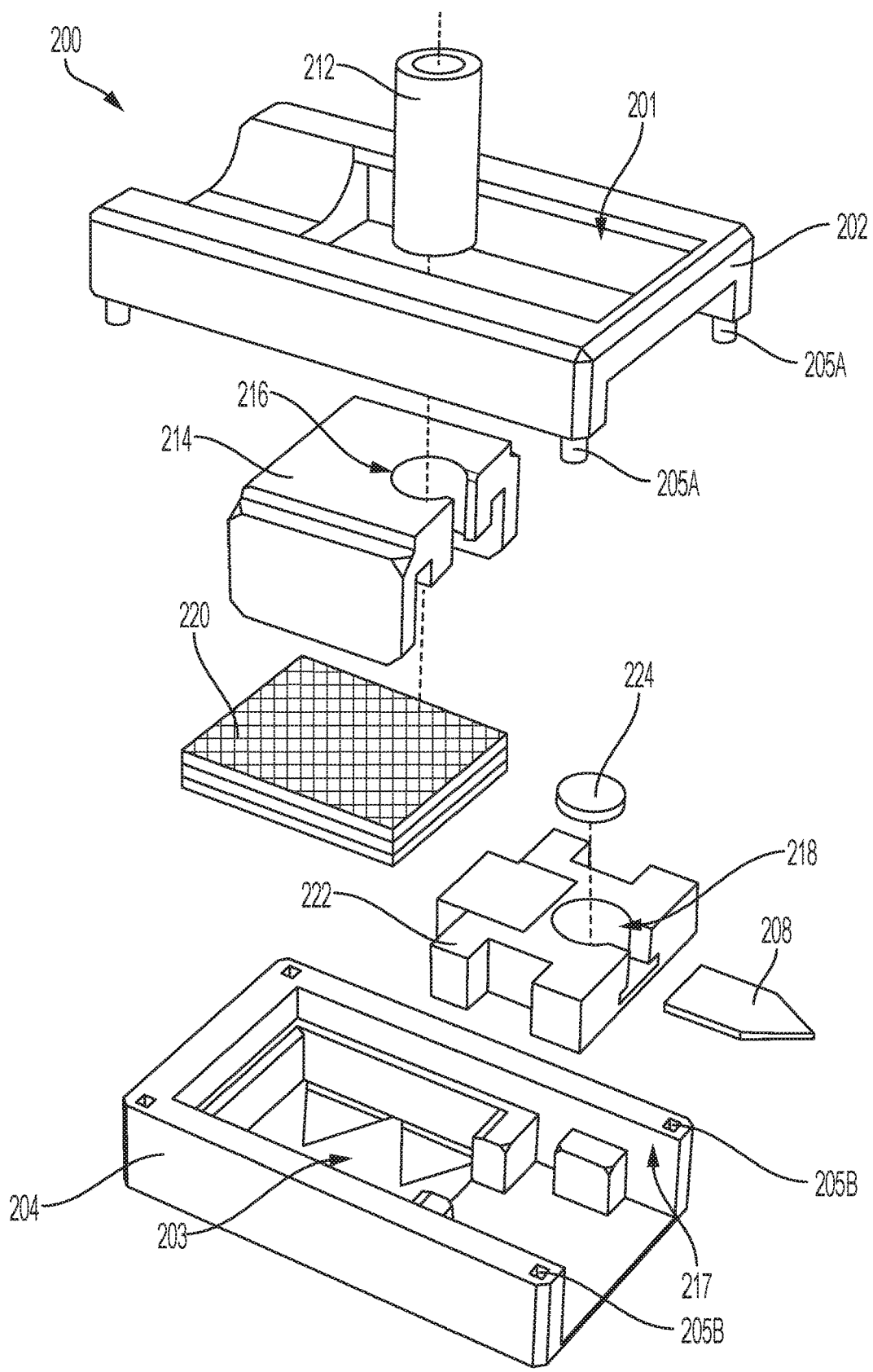
FIG. 4 is an exploded view of the cartridge of FIG. 3.

Referring now to FIGS. 3 and 4, a second cartridge 200 is shown. Cartridge 200 is generally used for protein digestion analysis. However, it is contemplated that cartridge 200 can be used for other methods of protein analysis (e.g., intact protein analysis). Cartridge 200 is otherwise substantially similar to cartridge 100 described above, with reference numerals of the cartridge 200 analogous to the reference numerals used in cartridge 100, except with 100 added thereto. As shown in FIG. 4, cartridge 200 further includes an enzyme immobilized membrane 224 that is positioned in recess 218 of holder 222. Enzyme immobilized membrane 224 functions to digest the peptides from the target proteins, which are then sent to a mass spectrometer 400 (FIG. 6) via spray tip 208 as described further below.

Similar to cartridge 100, all parts of cartridge 200 are assembled together, and column holder 214 slides along groove 217 between lid 202 and base 204 to switch the position of antibody column 212 from above waste pad 220, where the sample addition and washing steps occur, to above enzyme immobilized membrane 224 and spray substrate 208 where ionization by substrate supported electrospray ionization occurs.

Cartridges 100, 200 have a length ranging from 25 mm to 50 mm, or more particularly, from 30 mm to 40 mm. Cartridges 100, 200 have a width ranging from 10 mm to 50 mm, or more particularly, 20 mm to 30 mm. In one embodiment, cartridges 100, 200 have a length of 36 mm and a width of 22 mm.

Intact Protein Detection/Analysis

Figure 5:
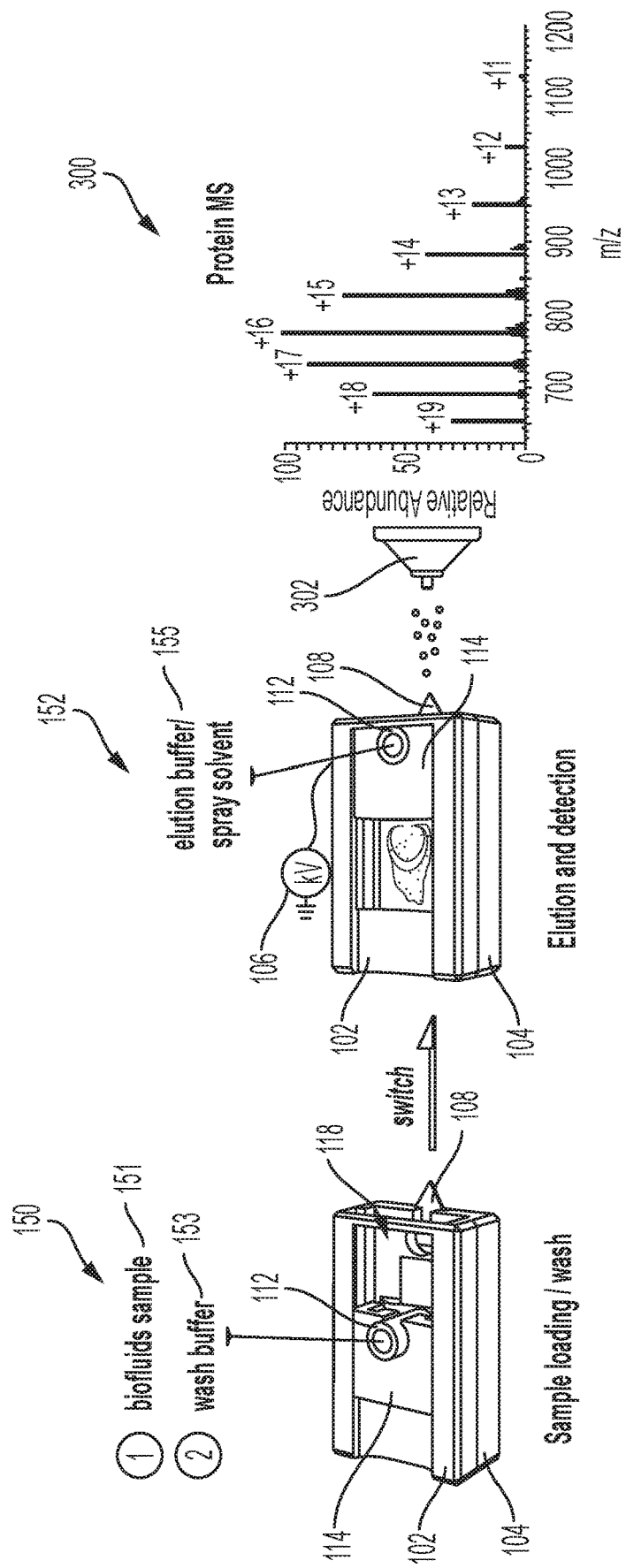
FIG. 5 is an illustration of the operation of the cartridge of FIG. 1 in connection with intact protein analysis.

Generally, for intact protein detection/analysis, a plasma sample is added to cartridge 100. The protein target is preconcentrated from the plasma sample using antibody coated latex beads. The protein target is then eluted from the beads using a solvent. Example solvents include: methanol:water 50:50 with 2% acetic acid or methanol:water 20:80 with 5% formic acid. The solvent, with the protein target dissolved, then passes onto a substrate which ionizes the protein for subsequent detection/identification by mass spectrometry via mass spectrometer 300 (FIG. 5).

Cartridge 100 provides a mass spectrometry cartridge designed for targeted detection of proteins from complex biofluids such as plasma. Selective enrichment of protein targets is performed on cartridge passively by capillary action and gravity with no pumping. Detection of the intact protein targets then proceeds via ionization of the protein target using a built-in spray substrate 108 consisting of carbon-nanotube (CNT) coated porous polyethylene. In another embodiment of built-in spray substrate 108, porous polyethylene is sputter coated with carbon to a thickness of about 100 nm. Sputter coating provides a more uniform and reproducible coating of the spray substrate 108. Cartridge 100 provides a simple, low cost approach to effectuate a combination of inexpensive lateral flow assays with mass spectrometry.

The detection efficiency of proteins by paper spray is relatively poor (a paper spray based immunoassay was reported in which a charged probe released from the bound antibody was detected by mass spectrometry (MS) (*J. Am. Chem. Soc.*, 2016, 138 (20), pp 6356-6359)). While this approach can have better sensitivity in some instances, because a small molecule is used for detection, the selectivity is ultimately limited by the antibody. Detection of the probe cannot give any information on the antigen such as post-translational modifications (PTMs). Improved protein ionization has been reported for paper coated with CNTs as well as size exclusion membranes, and carbon nanotube coated paper has been utilized for low voltage paper spray.

Figure 16:
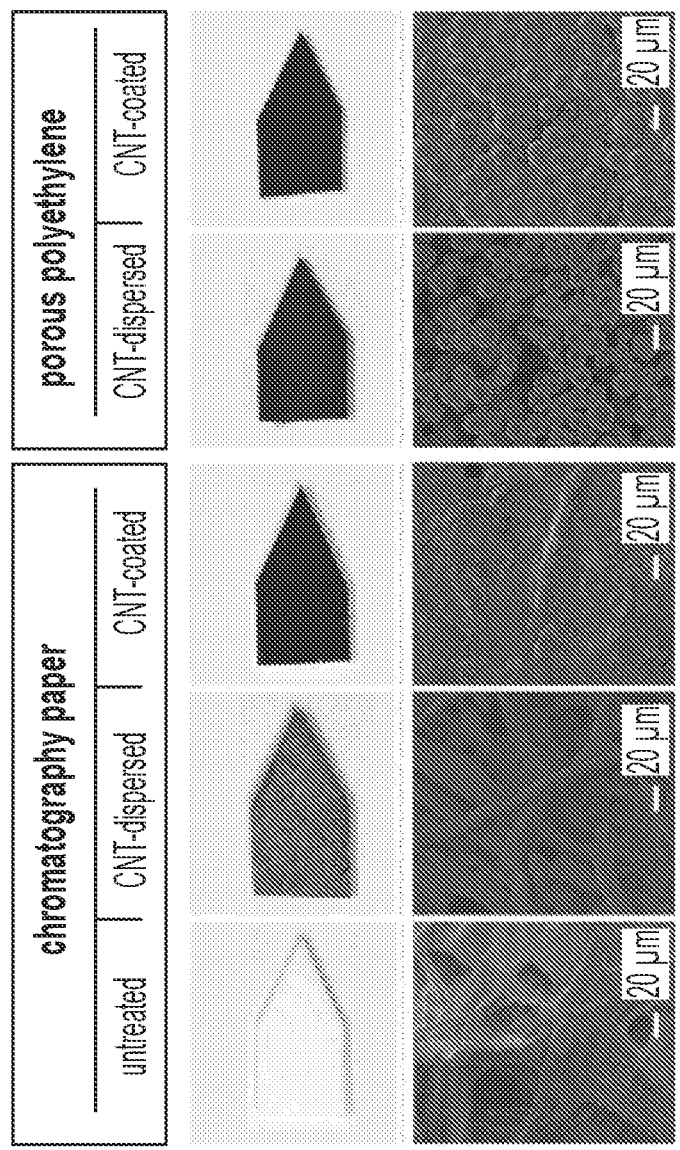
FIG. 16 is a photograph and SEM image of different spray substrates.

In the present disclosure, carbon nanotube (CNT) treated paper and CNT treated porous polyethylene (PE) have been examined for their ionization capabilities. Photographs and scanning electron microscope images of the spray substrates are shown in FIG. 16. In addition, as shown in Table 1 below, detection limits of three proteins were improved by coating or dispersing chromatography paper with single-walled CNTs.

TABLE 1

Limits of detection of protein obtained
by paper and PE spray substrates

| Spray substrates | | Detection limits (μg/mL) | | |
| --- | --- | --- | --- | --- |
| | | Cytochrome c | Myoglobin | Lysozyme |
| Paper | Untreated | 3 | 5 | 100 |
| | CNT-dispersed | 1 | 0.8 | 10 |
| | CNT-coated | 0.5 | 1 | 100 |
| PE | CNT-dispersed | 0.05 | 0.2 | 0.3 |
| | CNT-coated | 0.01 | 0.1 | 0.1 |

CNT-coated PE further improved protein detection; CNT-coated PE detection limits were between 8 and 100 times lower compared to the best obtained using CNT treated paper. As further shown in Table 1, detection limits of the protein standards were improved by a factor of 50-1000 compared to typical paper spray. Mass spectra obtained using paper and CNT-coated PE for a standard protein solution are shown in FIG. 18.

Figure 19:
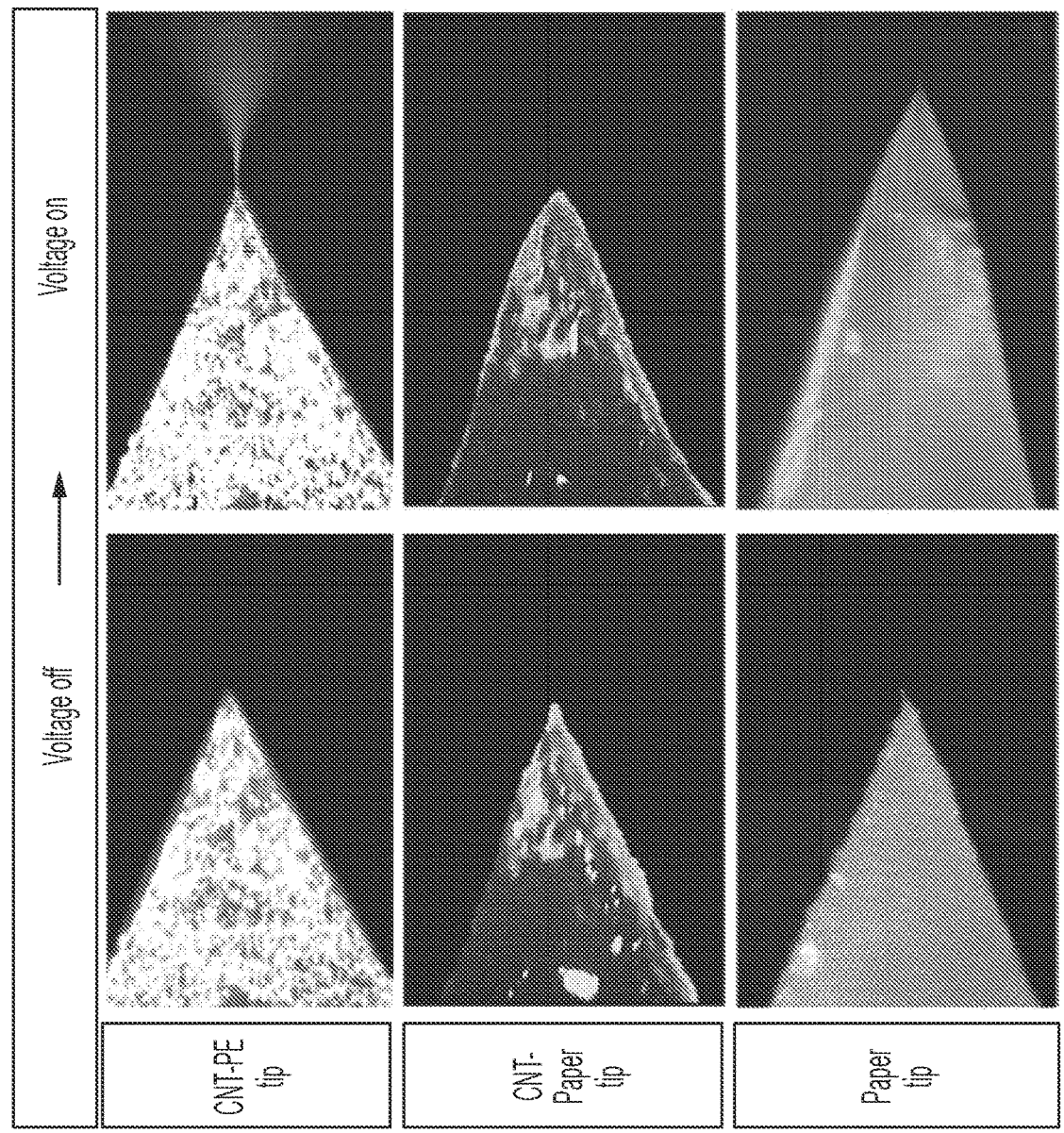
FIG. 19 shows pictures of three different substrates before and after application of high voltage for CNT-PE tip, CNT-coated paper tip, and paper tip.

As shown in FIG. 19, the Taylor cone generated from the CNT-coated PE tip was significantly smaller compared to paper. The size of the Taylor cone correlates with droplet size, and smaller electrospray droplets correlate with better ionization efficiency. The improved protein detection from the CNT coated PE substrate therefore may arise from balancing the surface energy of the substrate with that of the solvent to generate smaller droplets and more efficient ionization. The substrate needs to be sufficiently wettable to allow wicking by a polar solvent, necessary to drive fluid and analyte transport, but not so wettable that the Taylor cone is large. The CNT-PE substrate was also found to retain less protein than paper, but the difference was small compared to the improvement in detection limits.

To achieve selective and sensitive detection of target proteins from biofluids, an antibody column 112 integrated into cartridge 100 is used. In this method (referring to FIG. 5), protein preconcentration is performed using a membrane containing latex bead-antibody conjugates. At stage 150, a plasma sample 151 is added to antibody column 112 where the plasma sample flows through by a combination of capillary action and gravity. Excess sample 151 is absorbed into a built-in waste pad 120 in the bottom cartridge, while the part of the target protein in plasma sample 151 is retained on the latex bead conjugates. A washing step is also performed at stage 150 by subsequently adding a wash buffer 153 (e.g., water) to the preconcentration column, where the wash buffer 153 is wicked into waste pad 120. The protein analyte is then detected by sliding antibody column 112 to the elution position of stage 152 where the antibody column 112 is above spray substrate 108 and an elution buffer or spray solvent is added (e.g., 1:1 methanol/water with 2% acetic acid), which also acts as the extraction solution. As discussed in Example 2C further herein, over 90% of captured protein was eluted in the case of cytochrome c. Further discussion is provided in at least Examples 3-5 discussed herein.

Protein Digestion Analysis

Generally, for protein digestion analysis, a membrane 224 upon which proteolytic enzymes are immobilized is inserted between an antibody preconcentration step and the ionization step. This enzyme-coated membrane 224 digests the target protein into smaller peptide pieces. Ionization then proceeds by the same route as for intact protein work as described above and the sample is then sent for subsequent detection/identification by mass spectrometry via mass spectrometer 400 (FIG. 6).

Figure 6:
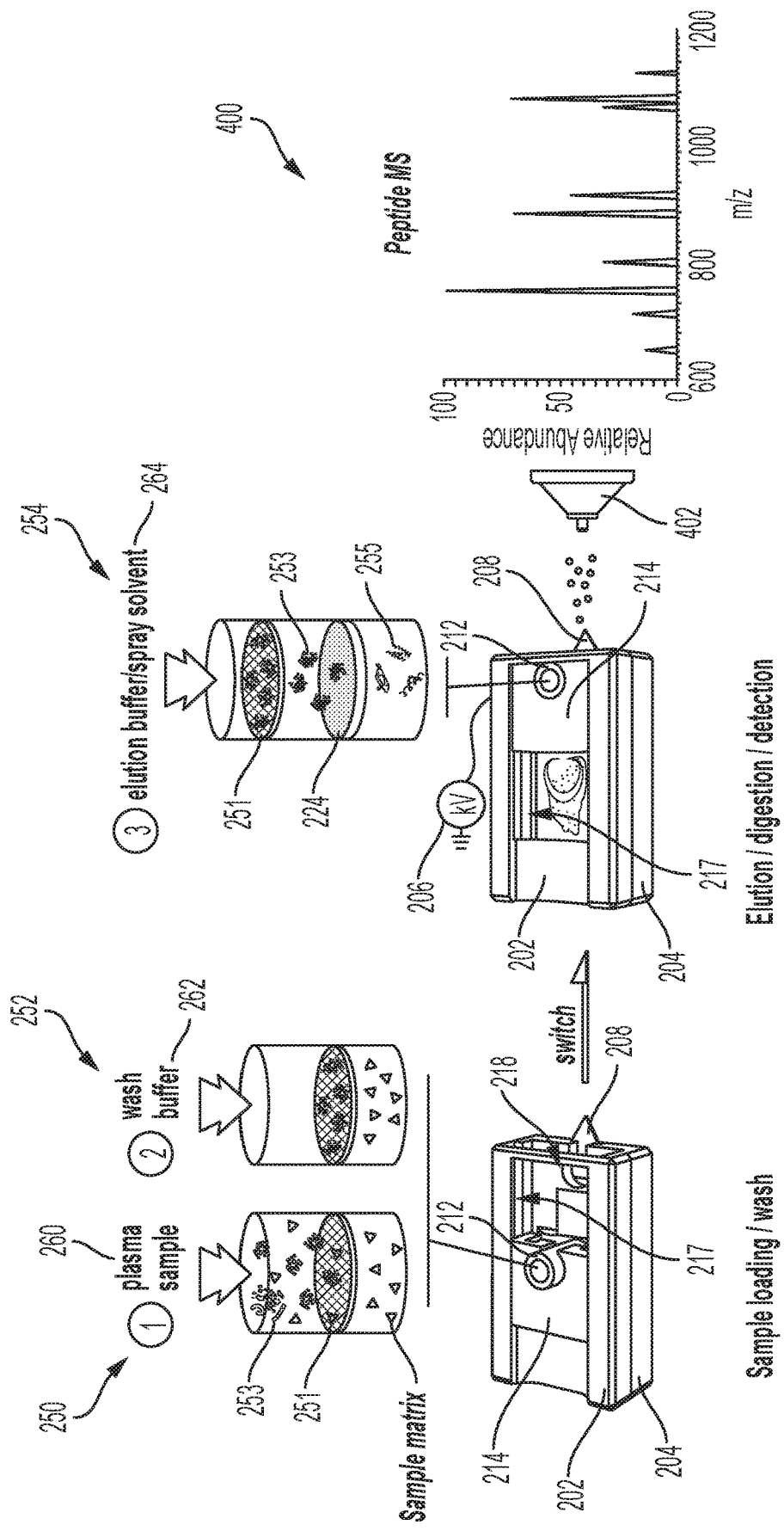
FIG. 6 is an illustration of the operation of the cartridge of FIG. 3 in connection with protein digestion analysis.

As shown in FIG. 6, at stage 250 diluted plasma samples 260 are added to the antibody column 212. Sample 260 is wicked through antibody column 212 and subsequently onto absorbent pad 220 contained within the bottom part of cartridge 200. As sample 260 passes through antibody column 212 within a specified period of time, target proteins 253 are retained on antibody column 212 via antibody coated membrane 251 while the excess matrix was absorbed onto waste pad 220. Then, as shown at stage 252, sample 260 that remained in the antibody column 212 was washed by applying a wash buffer 262 (e.g., deionized water) to antibody column 212; wash buffer 262 also wicks through column 212 onto absorbent pad 220. Target proteins 253 are recovered from antibody column 212 and analyzed by sliding column holder 214 (as well as antibody column 212) over and pushing antibody column 212 down into recess 218 so that antibody column 212 is in contact with enzyme immobilized membrane 224 and positioned above at least a portion of spray tip 208 rather than waste pad 220. Cartridge 200 is placed in front of an inlet 402 to mass spectrometer 400, and elution buffer/spray solvent 264 is added to enrichment column 212. Spray solvent 264 also serves as the extraction buffer and digestion buffer. Solvent 264 wicks through antibody column 212, recovering proteins in the process.

As the recovered proteins pass through the enzyme immobilized membrane 224, the target proteins 253 are digested into peptides 255. The peptide solution 255 then flows onto spray substrate (spray tip 208). Ionization was induced directly from the paper substrate by applying a high voltage (5 kV typically) to the CNT-PE tip through a wire 206 inserted from the side of cartridge 200. The cartridge is then placed in front of the inlet of mass spectrometer 400 for peptide identification.

Similar to cartridge 100, cartridge 200 provides a mass spectrometry cartridge designed for on-cartridge digestion of target proteins from complex biofluids such as plasma. Selective enrichment of protein targets is performed on cartridge passively by capillary action and gravity with no pumping. Enriched target proteins are eluted from the antibody coated membrane and then digested into peptides when passing through the enzyme immobilized membrane 224. Detection of the peptides then proceeds via ionization of the protein target using a built-in spray substrate consisting of carbon-nanotube (CNT) coated porous polyethylene. Cartridge 200 provides a simple, low cost approach to effectuate a combination of inexpensive lateral flow assays with mass spectrometry.

One advantage of protein digestion is that the process of the present disclosure combines the steps of antibody pre-preconcentration, digestion, and detection on a single cartridge. Additionally, the process provides detection of smaller peptides from the digested proteins that is more sensitive than detection via intact protein analysis since mass spectrometry (MS) is less effective at the detection of large molecules like proteins compared to smaller peptides. Furthermore, analysis of smaller peptides promotes flexibility in the instrumentation used as low resolution mass spectrometers (e.g., ion traps) may be used. Low resolution instruments work well for peptides because MS/MS or MS³ (tandem mass spectrometry) can be used to identify the peptides. MS/MS identifies the peptides by fragmenting the peptides, and a sequence can be determined from the MS/MS spectrum.

By contrast, for intact protein analysis, MS/MS is much less effective because the proteins analyzed are much larger, thereby requiring high resolution instruments (e.g., an orbitrap) for identification of the protein peaks. The advantage of using low resolution ion traps rather than orbitraps is that ion traps are much cheaper and much more robust in peptide identification. Furthermore, quantitative analysis of proteins can be more accurate and easily conducted with peptides than intact proteins.

Moreover, cartridge 200 enables targeted protein detection from plasma samples by mass spectrometry. Cartridge 200 allows for protein enrichment, digestion, and ionization to occur within one device—cartridge 200. Due to the simplicity of the analytical procedure in connection with cartridge 200, cartridge 200 better enables mass spectrometry based detection of protein targets which is applicable in clinical diagnostics and other fields.

EXAMPLES

Example 1

Preparation of Sample for Protein Digestion Analysis

To prepare a sample for protein digestion analysis, pepsin immobilization of a sample on a membrane was first conducted. 10 mL of a 0.02 M poly (styrene sulfonate) (PSS), 0.5 M NaCl solution (pH=2.3) was first passed through a 25-mm diameter nylon membrane at 2 mL/min. Then, 30 mL of deionized water was passed through the membrane at a flow rate of 2 mL/min. Subsequently, 4 mL of 2 mg/mL pepsin in 5% v/v formic acid (FA) was circulated through the membrane at 1 mL/min for 1 hour. After a protease deposition, the membrane was rinsed with 30 mL of 5% v/v FA for pepsin modification. The membrane was then allowed to dry, and stored at room temperature. Prior to testing, the membrane was cut to a diameter of about 5 mm discs.

After pepsin immobilization, offline protein digestion of the sample was conducted. In the Example, myoglobin was digested by passing through the pepsin immobilized nylon membrane. The digested sample was then collected into a plastic vial using a centrifuge, and the digested sample was then mixed with methanol at 1:1 v:v for ionization using a delrin cartridge with a carbon nanotube coated polyethylene (CNT-PE) tip.

Target proteins in the sample are extracted, digested, and then ionized using digestion cartridge 200 as shown in FIG. 6. As shown in FIG. 6, the diluted human plasma samples (1:10 dilution, 20 μL plasma diluted with 180 μL deionized water) were added to the antibody column 212. The sample wicked through antibody column 212 and subsequently onto absorbent waste pad contained within the bottom part of cartridge. As the sample passed through the antibody column (within 5 minutes), target proteins were retained on the antibody column 212 via an antibody coated membrane 251 while the excess matrix was absorbed onto the waste pad. The sample was then washed by applying 400 μL of deionized water to antibody column 212; the deionized water also wicked through column onto the absorbent pad. The target proteins were recovered from antibody column 212 and analyzed by sliding the column holder 214 (as well as antibody column 212) over and pushing antibody column 212 down into a recess so that antibody column 212 was in contact with the enzyme immobilized membrane 224 (positioned above the pentagon-shaped CNT-PE substrate 208) rather than the waste pad. Cartridge was placed in front of an inlet to the mass spectrometer, and the spray solvent (typically 20:80 methanol:water with 5% acetic acid) was added to the top of the enrichment column. The spray solvent also served as the extraction buffer and digestion buffer. The solvent wicked through the antibody column, recovering the proteins in the process.

As the recovered proteins passed through enzyme immobilized membrane 224, the protein sample was digested into peptides. The peptide solution then flowed onto the spray substrate 208 (spray tip 208). Ionization was induced directly from the paper substrate by applying a high voltage (5 kV typically) to the CNT-PE tip through a wire inserted from the side of cartridge. Peptides are identified in the following mass spectrometry analysis and data process.

Example 1A—Spectrum Obtained Using Pepsin Immobilized Membrane

Figure 7:
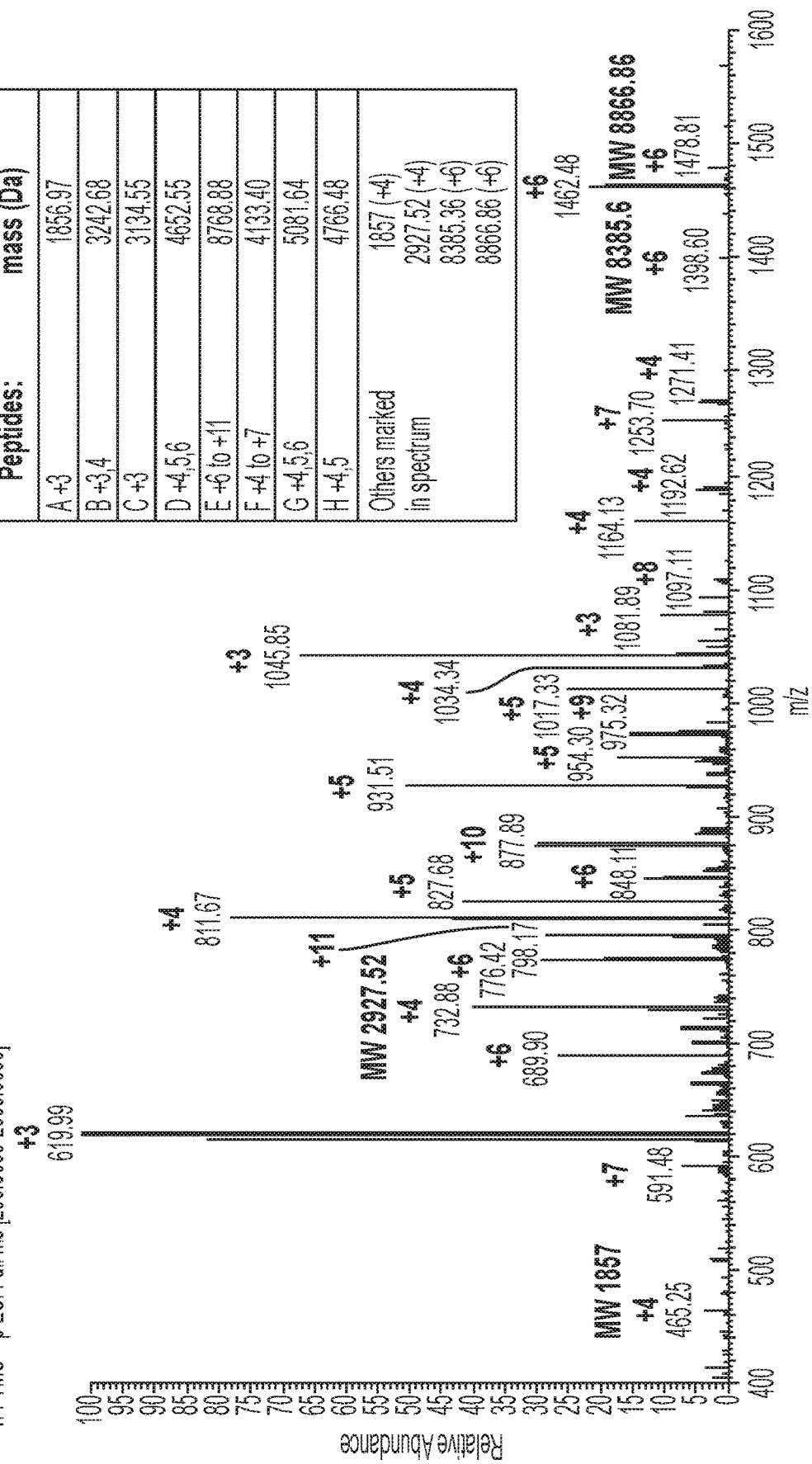
FIG. 7 is related to Example 1A and provides the peptide data from the mass spectrum and insert table provided.

A dozen peptides from the myoglobin digestion were identified from the spectrum as shown in FIG. 7. Details of the peptides are marked in the figure and the insert table. No intact protein signals were observed, indicating that nearly all of the intact protein was digested by the immobilized enzyme.

Example 1B—Effect of Membrane Pore Size on Protein Digestion

Figure 8A:
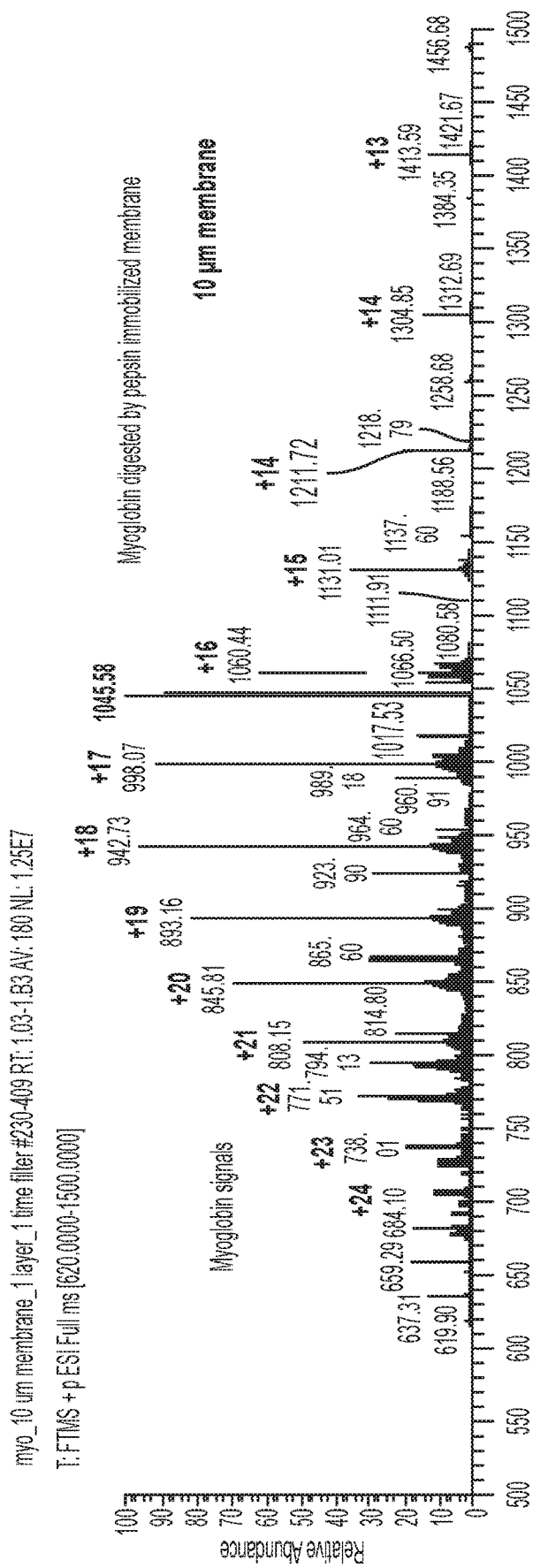
FIG. 8A is related to Example 1B and provides the mass spectra data for peptides obtained using a 10 μm pore size membrane.
Figure 8B:
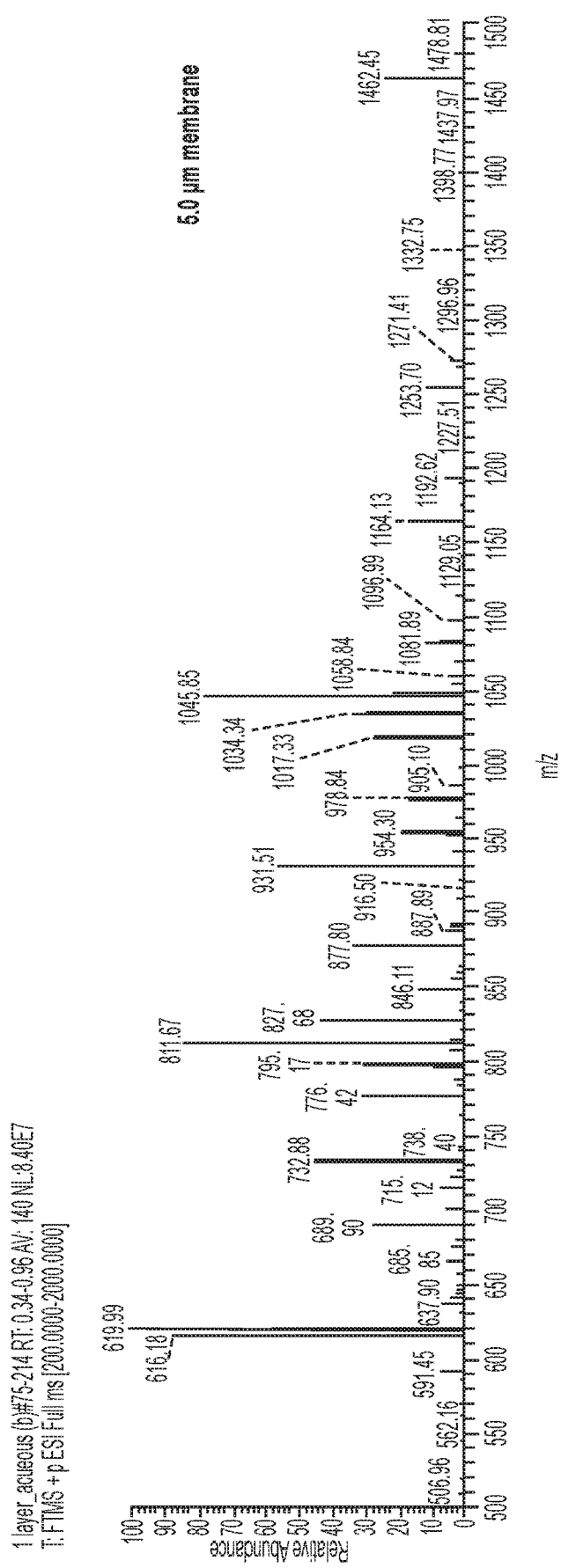
FIG. 8B is related to Example 1B and provides the mass spectra data for peptides obtained using a 5.0 μm pore size membrane.
Figure 8C:
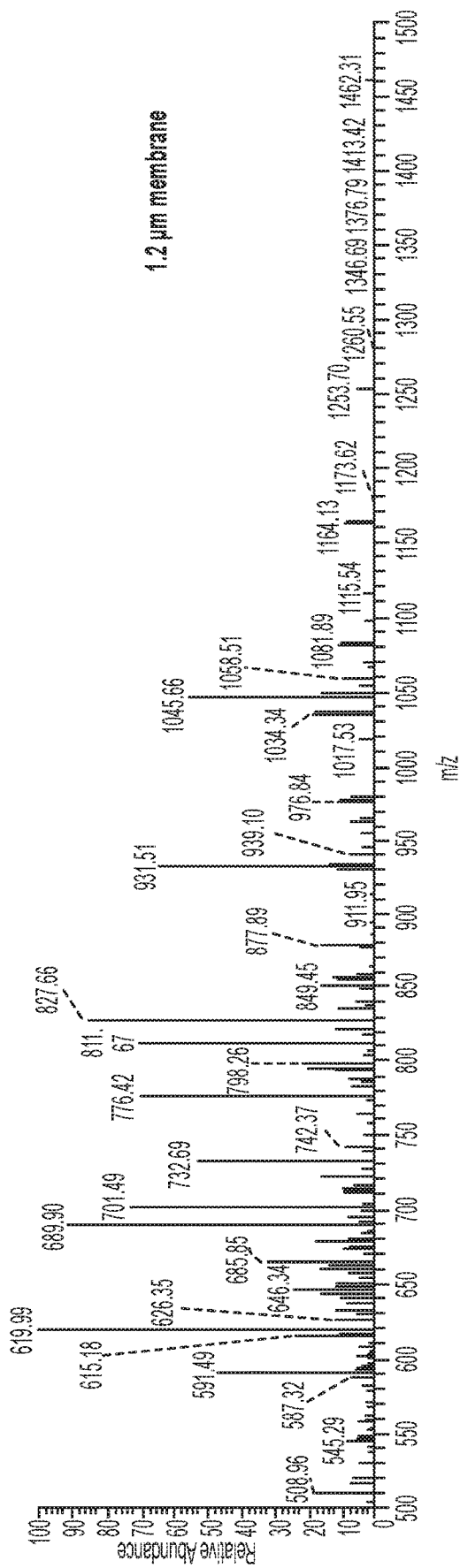
FIG. 8C is related to Example 1B and provides the mass spectra data for peptides obtained using a 1.2 μm pore size membrane.

Spectra obtained from the use of 10 μm, 5.0 μm, and 1.2 μm membranes are shown in FIGS. 8A-C, respectively. Digestion efficiency increased with smaller membrane pore size. In addition, a greater number of peptides with higher intensities were observed using smaller pore size membrane. Protein signals were observed in the 10 μm membrane spectrum. Similar peptides were shown in the 5.0 μm and 1.2 μm membrane spectra. However, the intensities of larger peptides (such as m/z 1462, MW 8.7 kDa) decreased in 1.2 μm membrane spectra, indicated that smaller pore size offer more complete digestion.

Example 1C—Use of Methanol Solution as Digestion Buffer

Figure 9A:
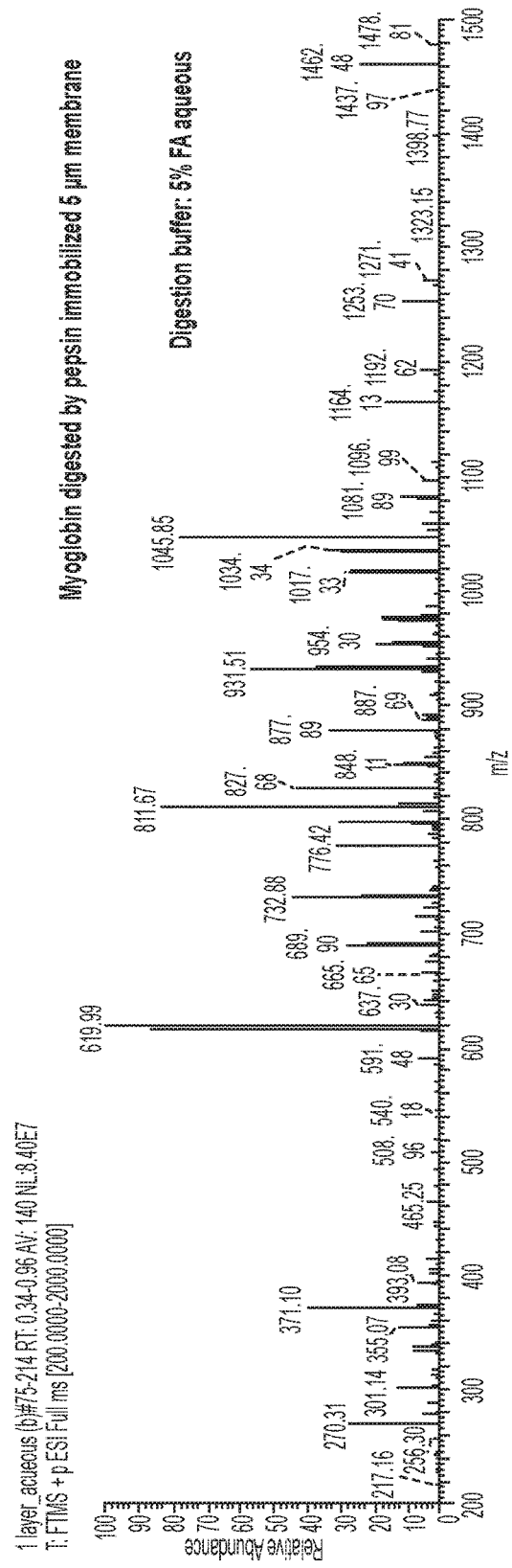
FIG. 9A is related to Example 1C and provides the mass spectra data for peptides obtained using a 5% formic acid aqueous digestion buffer with a 5 μm pore size membrane.
Figure 9B:
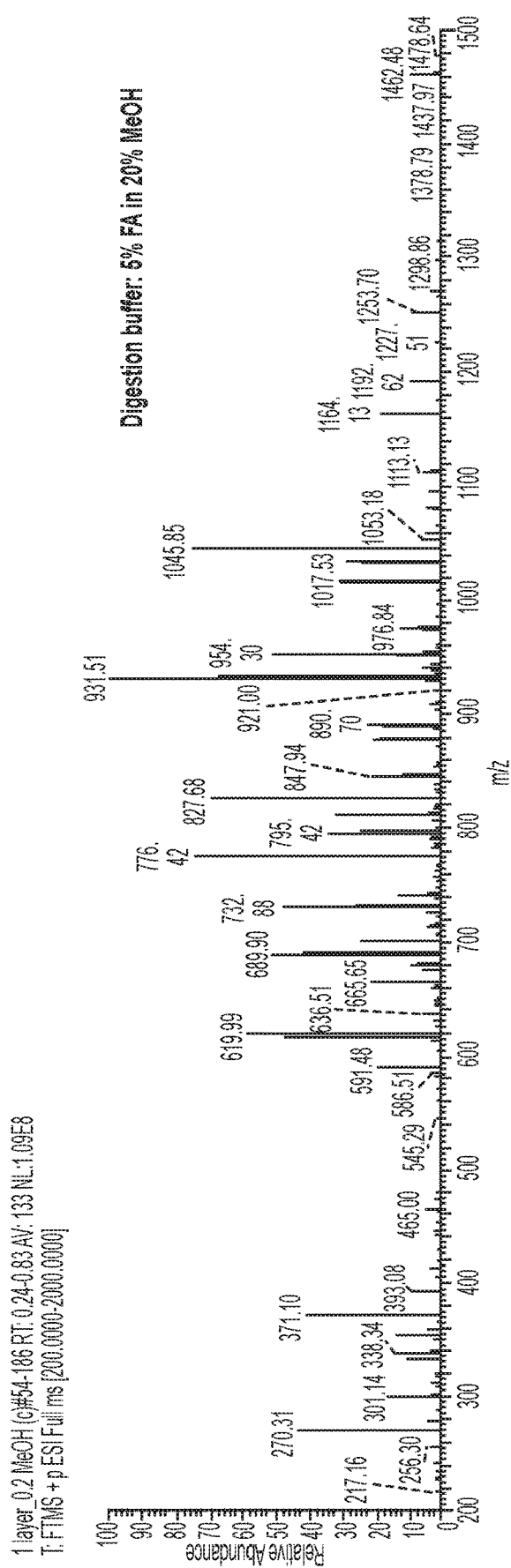
FIG. 9B is related to Example 1C and provides the mass spectra data for peptides obtained using a 5% formic acid in 20% methanol digestion buffer with a 5 μm pore size membrane.

In this Example, as shown in FIGS. 9A and 9B, 20% and 50% methanol solutions were tested as digestion buffers for the membrane experiments. FIGS. 9A and 9B show the spectra obtained from 5 μm membrane using aqueous solution and 20% methanol as digestion buffer. As shown, no digestion occurred in 50% methanol buffer, which is similar to the in-solution experiment. However, the 20% methanol solution worked as well as the aqueous digestion buffer in the membrane digestion.

As determined from FIGS. 9A and 9B, 20% methanol with 5% formic acid is an effective solvent for both the digestion step and the ionization step. Having some methanol present in the digestion buffer provides for a more effective ionization step due to its polarity. Stated another way, the ionization step is less effective without some polar organic solvent such as methanol or acetonitrile.

Figure 10A:
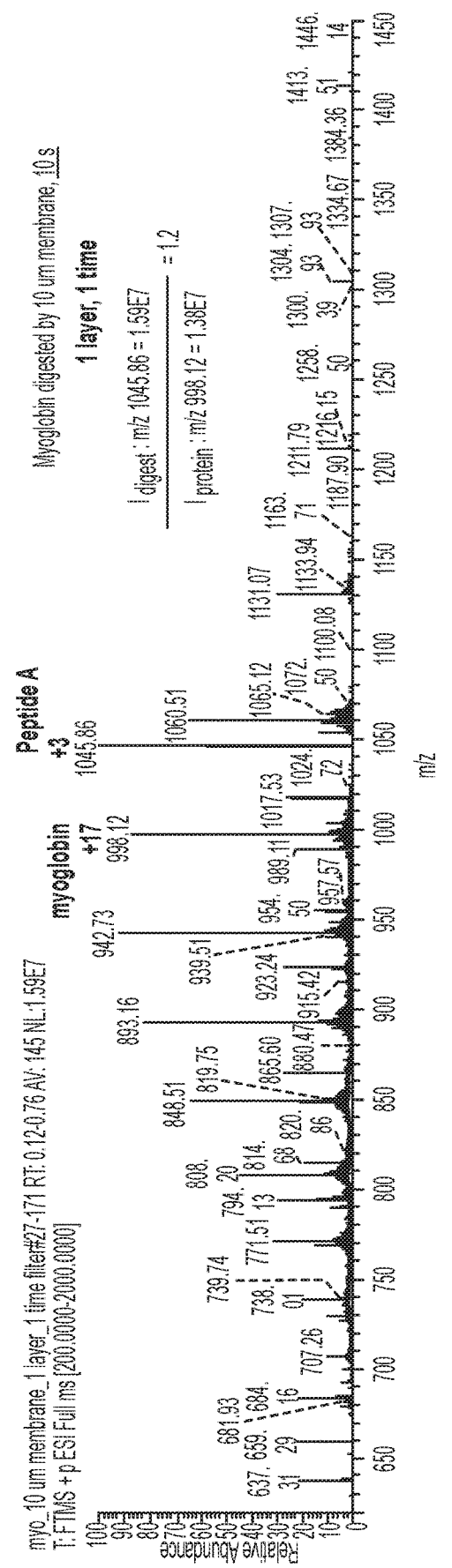
FIG. 10A is related to Example 1D and provides mass spectra data for myoglobin digested by a 10 μm membrane and having a digestion time of 10 seconds.
Figure 10B:
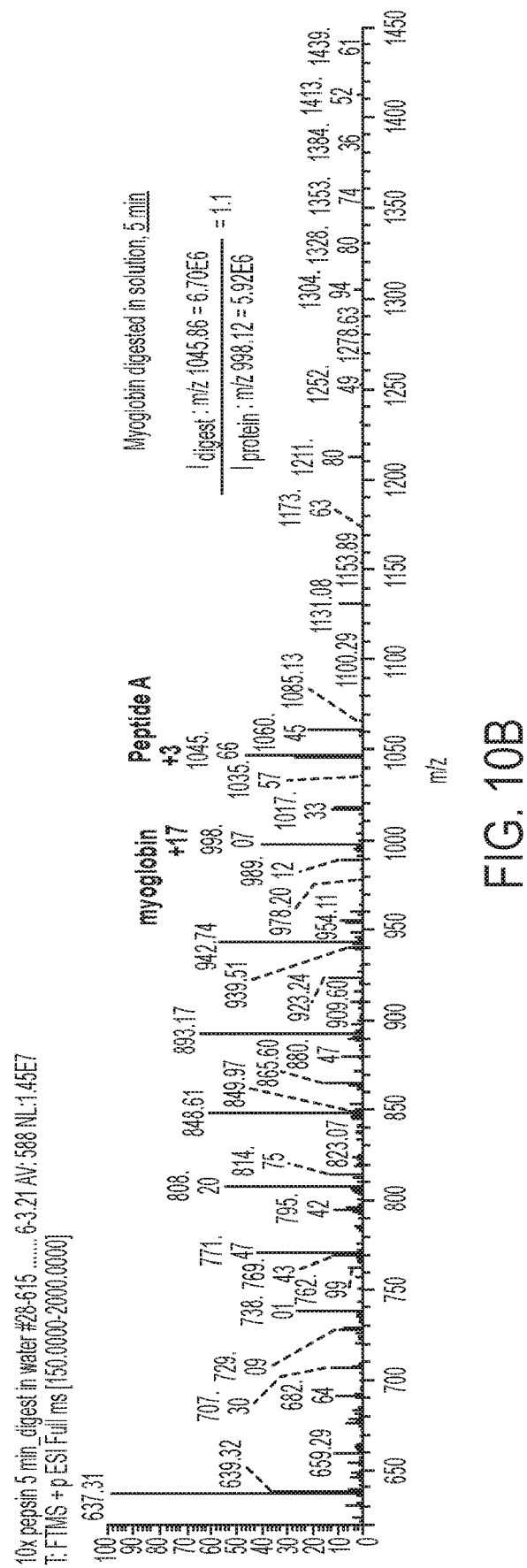
FIG. 10B is related to Example 1D and provides mass spectra data for myoglobin digested in solution having a digestion time of 5 minutes.

Example 1D—Digestion Efficiency was Significantly Improved by Using the Immobilized Membrane The spectra shown in FIGS. 10A and 10B were obtained from the sample digested by immobilized membranes and in solution experiments. In comparison with in solution digestion, the immobilized membrane gave a similar I digest/I protein ratio. However, the digestion time was reduced from 5 min to 10 s. Thus, the digestion efficiency improved. In addition, immobilized membrane was compatible with MS cartridge for the on-line digestion.

Example 1E—Spectrum Obtained Using Pepsin Immobilized CNT-PE Tip

Figure 11:
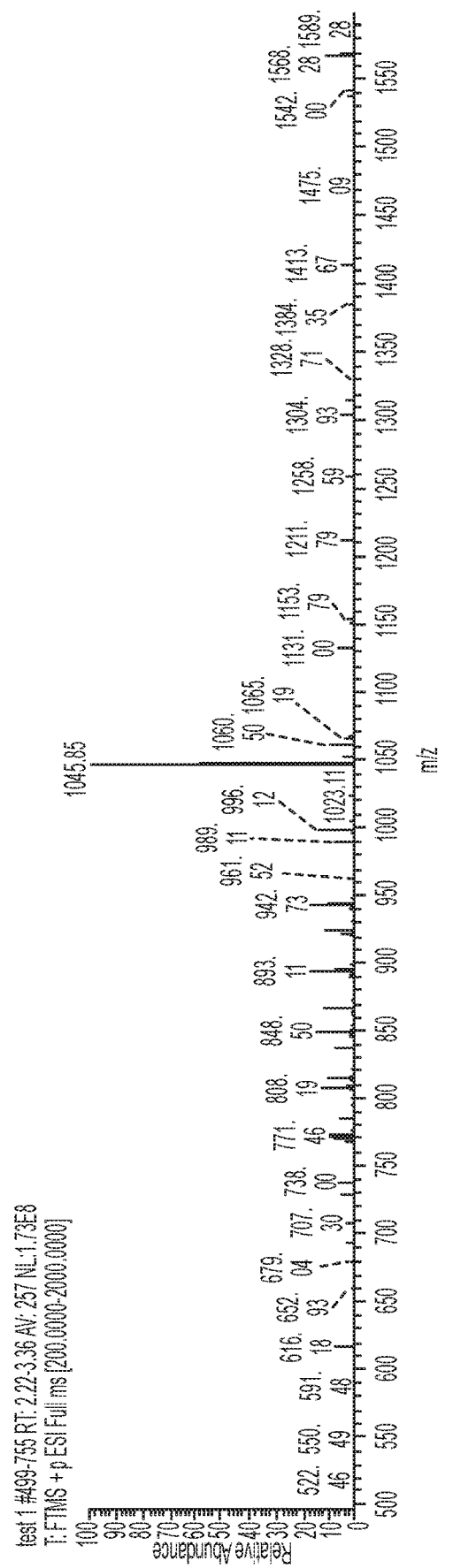
FIG. 11 is related to Example 1E and shows the mass spectra data obtained using a pepsin immobilized carbon nanotube coated polyethylene (CNT-PE) tip.

In this Example, a non-covalent method "electrostatic interaction" was tested. It is also the method used to immobilize pepsin onto nylon membranes. FIG. 11 shows the spectrum obtained using a pepsin immobilized CNT-PE tip. Myoglobin solution was directly added onto and sprayed from the spray tip. The base peak at m/z 1045.85 (+3) was a peptide digested from myoglobin. Myoglobin signals can also be observed in this spectrum, such as m/z 893, m/z 942, and m/z 998.

The peptide species identified from this spectrum were much less than that of on membrane digestion, which was 12 peptides. In general, this spectrum looks like an in solution digestion spectrum. The digestion efficiency was significantly lower than that of on membrane digestion. Three digestion methods have been tested for digestion efficiency [in-solution (5 min), on membrane (~10 s), and on spray tip (immediately)], and the rank of digestion efficiency is: on membrane>>on CNT-PE tip>=in-solution.

Example 1F—Spectrum Obtained Using Pepsin Coated CNT-PE Tip

Figure 12A:
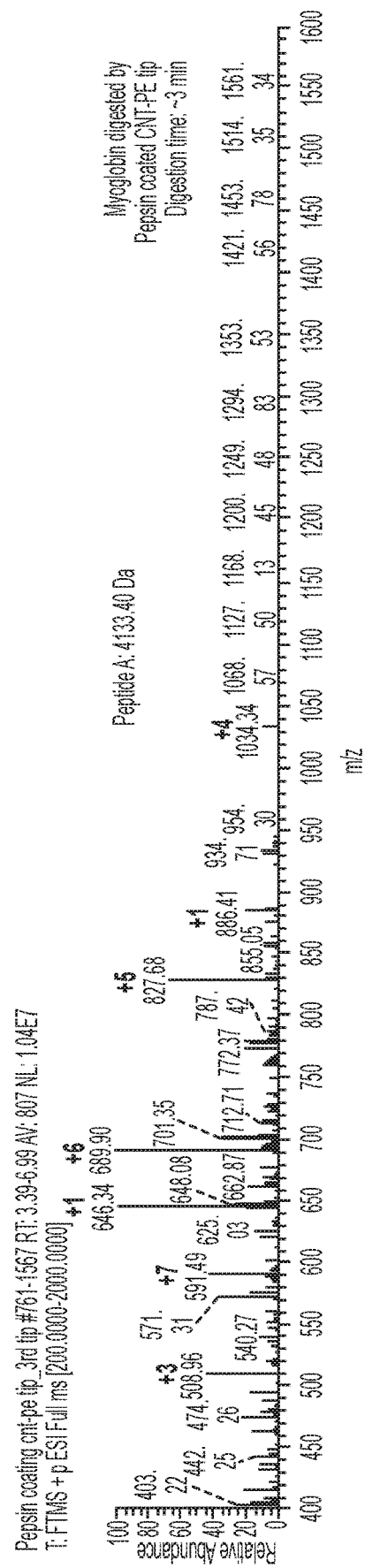
FIG. 12A is related to Example 1F and shows the mass spectra obtained using a pepsin coated CNT-PE tip.
Figure 12B:
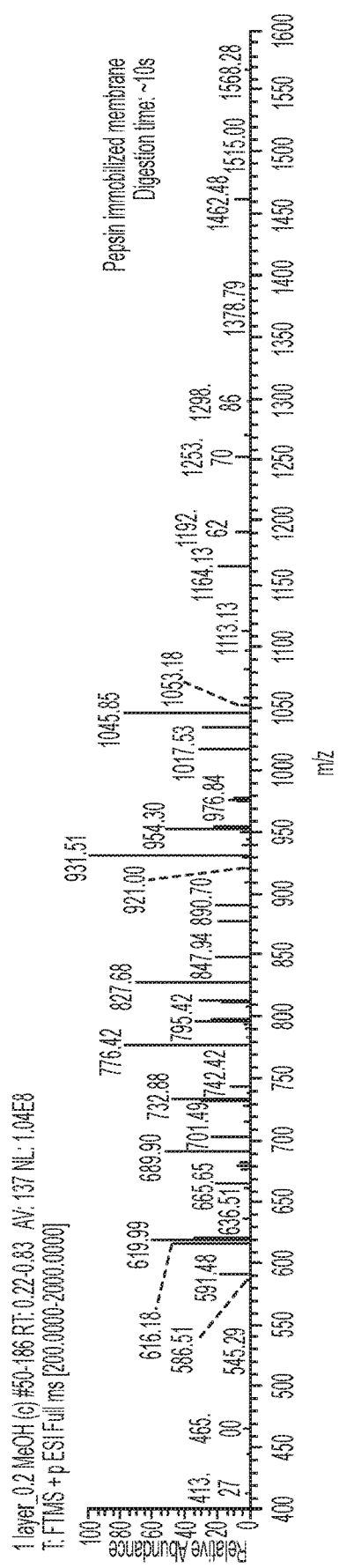
FIG. 12B is related to Example 1F and shows the mass spectra obtained using a pepsin immobilized membrane.

FIGS. 12A and 12B show the spectra obtained using a pepsin coated CNT-PE tip and a pepsin immobilized membrane, respectively. No myoglobin signals observed in both spectra indicated a high digestion efficiency of pepsin digestion. Pepsin immobilized membrane spectrum (FIG. 12B) was processed as described previously and 12 species of peptides were identified. The peptide signals in pepsin coated tip spectrum (FIG. 12A) were found in a relative lower m/z range.

Example 1G—Spectrum Obtained Using Pepsin Immobilized 5 μm Nylon Membrane

Figure 13A:
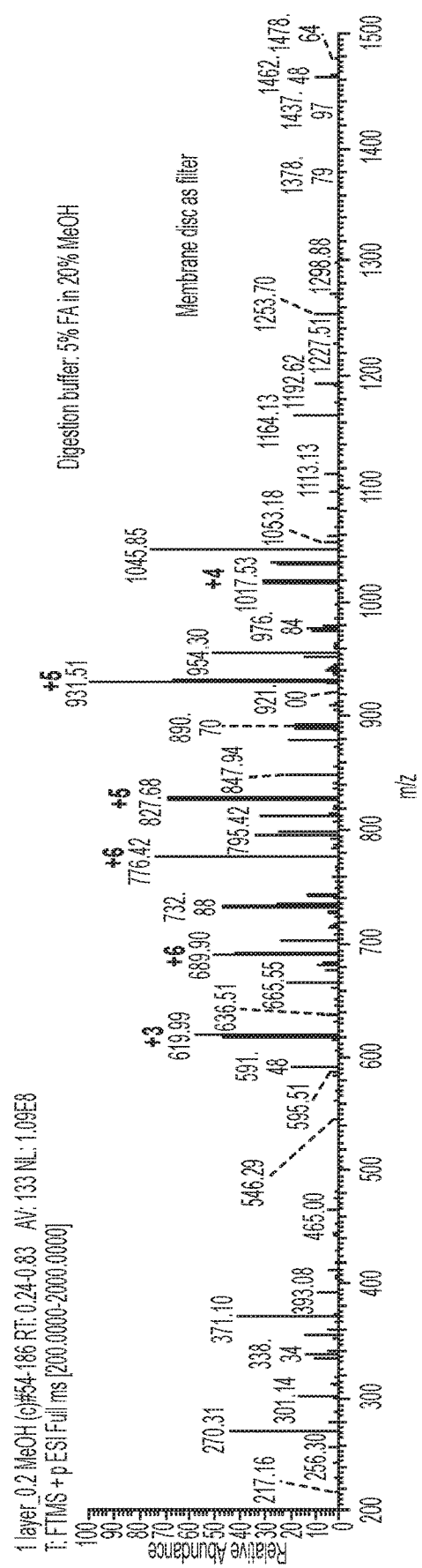
FIG. 13A is related to Example 1G and shows the mass spectra data using a pepsin immobilized membrane as filter.
Figure 13B:
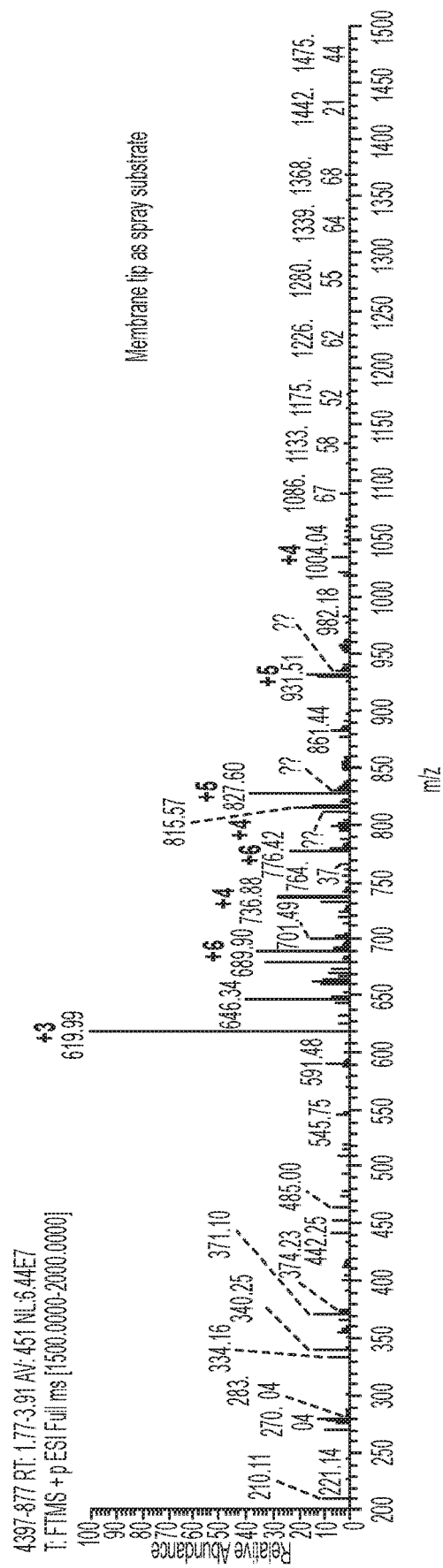
FIG. 13B is related to Example 1G and shows the mass spectra data using a membrane tip as spray substrate.

A pepsin immobilized 5 μm nylon membrane was cut to a spray tip and used for direct analysis of the myoglobin sample. The following spectra shown in FIGS. 13A and 13B demonstrated the differences between using the enzyme immobilized membrane disc as a filter (FIG. 13A) and using the enzyme immobilized membrane tip as spray substrate (FIG. 13B).

Using the membrane as a spray tip resulted in fewer peptide species and lower intensity, especially for the peptides of larger molecular weights. As shown, FIGS. 13A and 13B marked the 3 kind of peptides identified in both spectra. In FIG. 13A, 9 other kinds of peptides can be identified.

Example 1H—in Solution Digestion Data

Figure 14A:
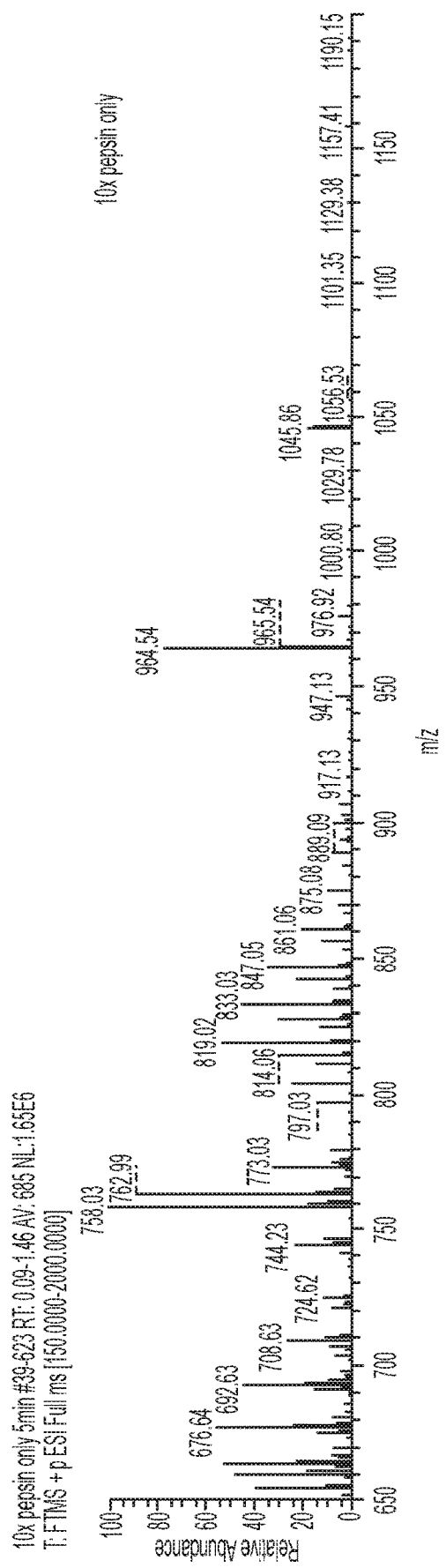
FIG. 14A is related to Example 1H and shows the mass spectra data of a pepsin only sample.
Figure 14B:
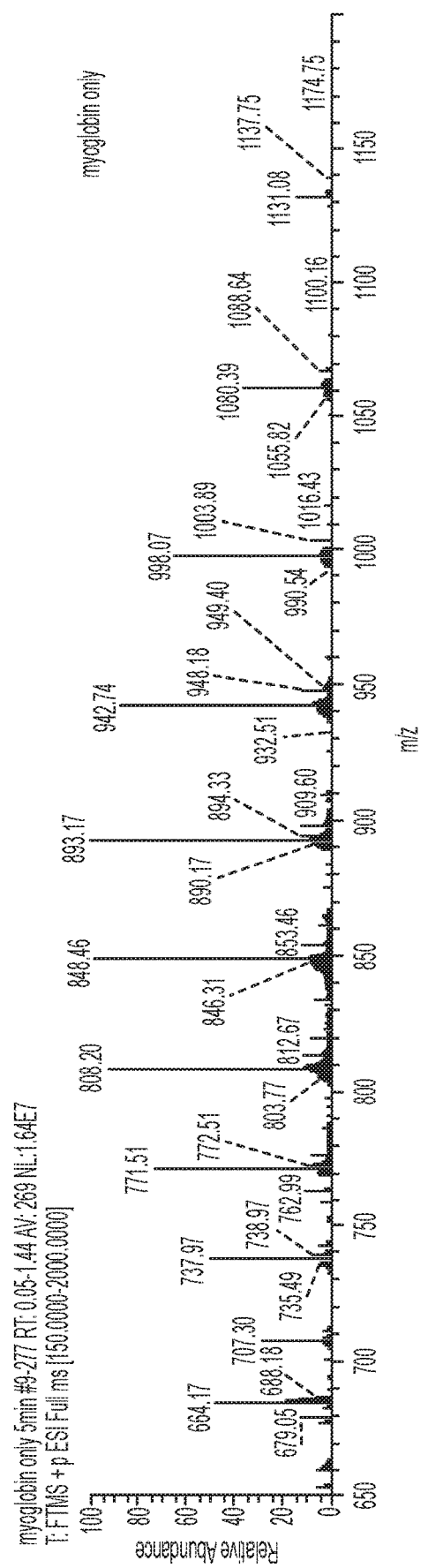
FIG. 14B is related to Example 1H and shows the mass spectra data of a myoglobin only sample.
Figure 14C:
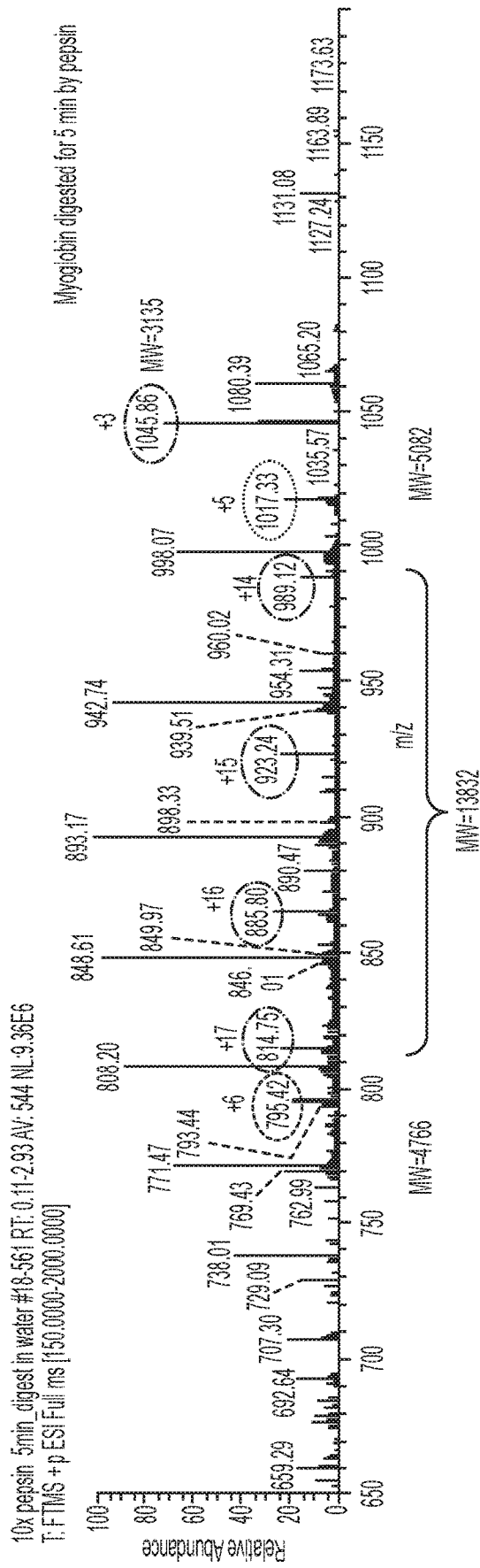
FIG. 14C is related to Example 1H and shows the mass spectra data of a myoglobin digested for 5 minutes by pepsin sample.

The spectra shown in FIGS. 14A-C are of pepsin only, myoglobin only, and myoglobin digested for 5 minutes by pepsin, respectively. In comparison with the pepsin only spectra (FIG. 14A) or the myoglobin only spectrum (FIG. 14B), spectrum for myoglobin digested for 5 minutes by pepsin (FIG. 14C) shows some additional peaks. These peaks can be attributed to some protein fragments/peptides as marked in the figure.

Example 1I—Influence of Methanol Proportion on Pepsin Activity

Figure 15A:
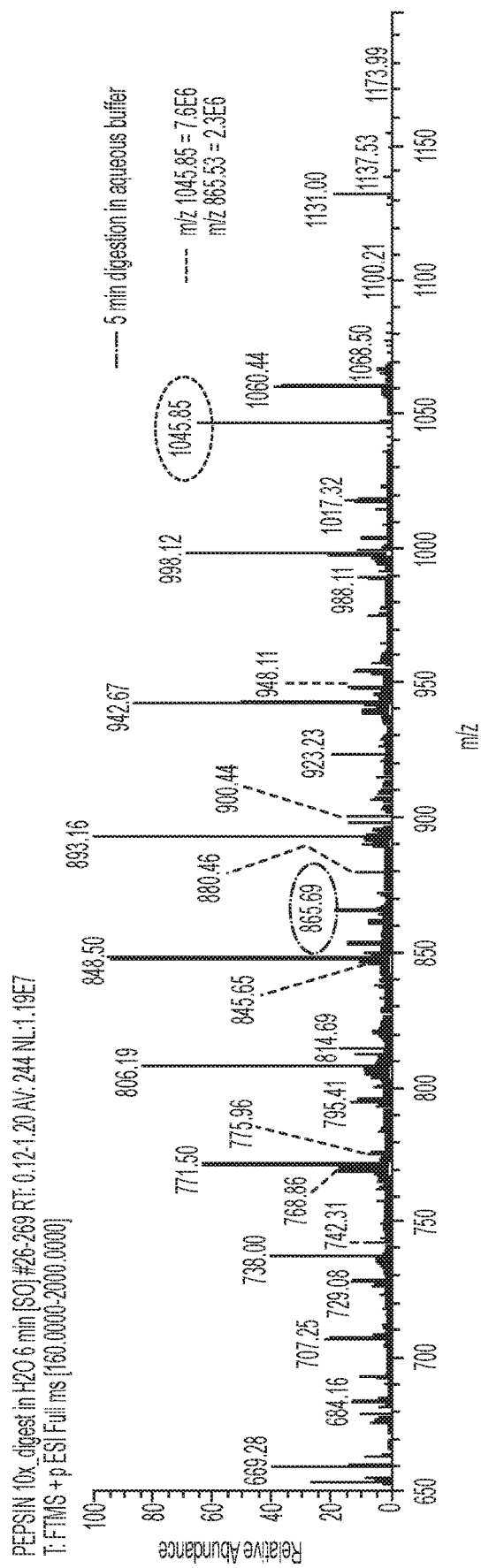
FIG. 15A is related to Example 1I and shows the mass spectra data of a sample obtained from pepsin digestion in an aqueous buffer.
Figure 15B:
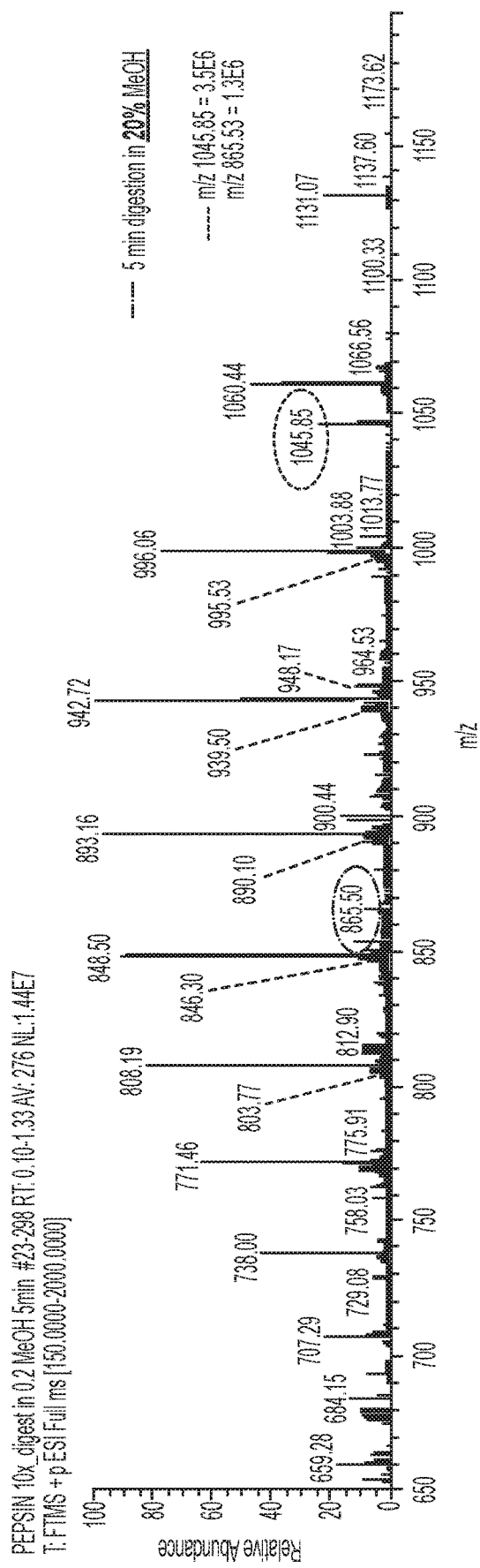
FIG. 15B is related to Example 1I and shows the mass spectra data of a sample obtained from pepsin digestion in a 20% methanol buffer.
Figure 15C:
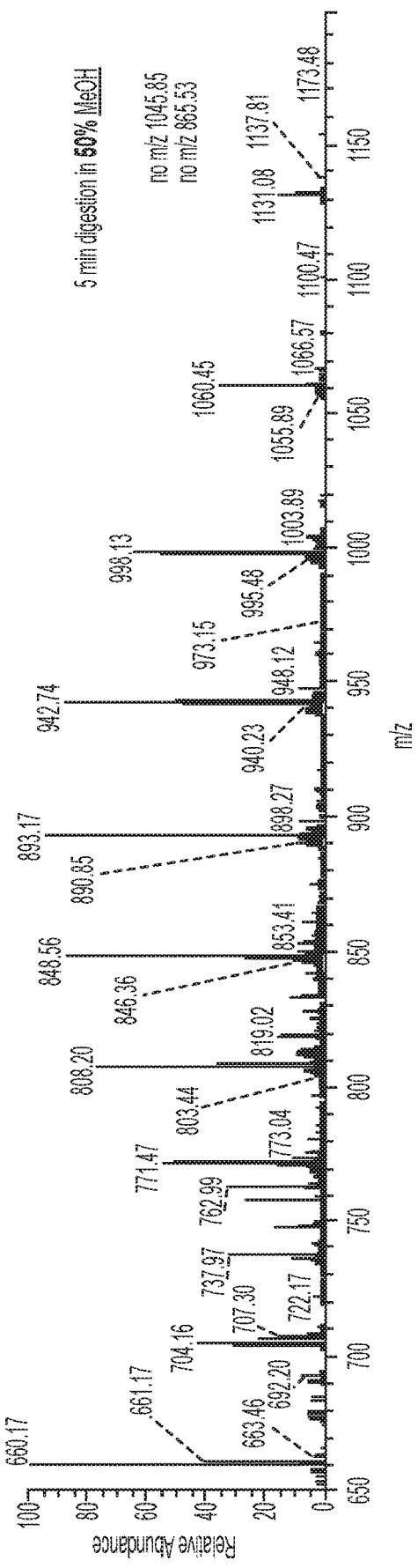
FIG. 15C is related to Example 1I and shows the mass spectra data of a sample obtained from pepsin digestion in a 50% methanol buffer.

The following spectra shown in FIGS. 15A-C were obtained from pepsin digestion in aqueous buffer, 20% MeOH buffer, and 50% MeOH buffer, respectively. Intensities of two characterization ions m/z 1045.85 and m/z 865.53 was shown.

In comparison with aqueous digestion (FIG. 15A), 20% MeOH digestion sample (FIG. 15B) was shown to have about half intensities for both ions. By contrast, none of the ions can be observed from 50% MeOH digestion sample (FIG. 15C).

Example 2

Pretreatment of carbon nanotubes (CNT). The single-walled carbon nanotube powder was washed by immersion in methanol:water 1:1 (v:v) and sonication for 15 minutes (3×), followed by immersion in pure methanol and sonication for 15 minutes (3×), and then stored in pure methanol as a slurry with a concentration of about 10 mg/mL.

Preparation of porous polyethylene (PE). The PE was cut into rectangles (2.0 cm×0.5 cm) and then washed by immersion in pure methanol and vortexing for 1 minute (3×) and followed by immersion in 1:1 methanol:water and vortexing for a minute (3×). The washed PE was then allowed to dry before applying CNT.

Preparation of CNT-dispersed spray substrates. The spray substrates, chromatography paper, and porous polyethylene were immersed in the CNT slurry and sonicated for 30 minutes. CNT-dispersed spray substrates were allow to dry and cut into pentagon shape with a sharp tip, as shown in FIG. 16.

Preparation of CNT-coated spray substrates. The paper substrate and washed thin piece of PE were placed on an absorbent pad, and the CNT slurry (10 mg/mL in methanol) was pipetted onto the upper surface of spray substrates. After the solvent passed though the spray substrate to the absorbent pad, most of the CNT stay on the surface of spray substrates. CNT-coated paper substrate was ready to use after drying and cut into pentagon shape with a sharp tip. Additional treatment was applied to the CNT-coated PE after drying. Specifically, the upper surface was polished with a wipe to remove the excess CNT and form a thin CNT-coated layer on the PE substrate, and then washed again as described in the preparation of porous polyethylene. The CNT coated PE substrate was allowed to dry, then cut into spray tips. To form the spray tip, one side of the rectangle (short side) was cut evenly to a fine triangular point.

Preparation of antibody coated membrane. To prepare the antibody coated membrane, the antibodies were coated onto carboxyl latex beads, the protocol for prepare antibody coated membrane (4 pieces) was as described below. The antibody and buffer was warmed to room temperature prior to use.

Carboxyl latex preparation. 50 μL (40 mg/mL, 1.4 μm diameter) latex microspheres was pipetted and diluted with 150 μL MES buffer. Then, the mixture was centrifuged for 3000 revolutions per minute (rpm) for 5 minutes to sediment the particles. The supernatant was then removed and the pellet re-dispersed in 150 μL IVIES buffer. The mixture was then centrifuged again and the supernatant was removed from the particles. The pellet was then re-suspended in 100 μL IVIES buffer by vortexing to ensure a completely suspend of the microsphere particles.

Preparation of Antibody-Labeled Latex Beads.

Preparation of antibody labeled latex beads are provided in the steps below:
1. Add 10 mg 1-Ethyl-3-(3-dimethylaminopropyl)carbodiimide (EDAC) powder into the latex suspension prepared above, and react for 15 min with constant vortex to activate the latex beads.
2. Centrifuge the mixture to sediment the activated latex beads: 3000 rpm for 5 min.
3. Remove supernatant and re-disperse the pellet in 100 µL IVIES buffer.
4. Centrifuge again and remove the supernatant from the particles.
5. Repeat step 3-4 twice more for a total of 3 washes.
6. Re-suspend activated latex beads in 50 µL MES buffer by vortexing to ensure a completely.
7. Add an antibody solution (1 mg/mL, 250 µL, 10× excess) to the latex suspension prepared above. For the antibody solutions that contain sodium azide, the solutions were treated by centrifuge filters to remove the azide prior to binding the antibody to latex beads.
8. Incubate latex/antibody mixture with gentle mixing at room temperature for 5 hours.
9. Centrifuge to separate the antibody-labeled latex beads from unbound antibody solution.
10. Remove ad retain supernatant for the preparation of more antibody-labeled latex beads.
11. Re-suspend the beads in 100 µL PBS buffer.
12. Centrifuge again to sediment the beads.
13. Repeat steps 11-12 twice more for a total of 3 washes.
14. Re-suspend the final latex beads in 100 µL PBS buffer with 0.1% glycine. Store at 4° C. until use.

Coat the antibody-labeled latex beads onto the glass-fiber membrane: Several 3-mm diameter glass fiber filter membranes (1.2 µm retention) were placed on an absorbent pad. The re-suspended final latex bead was pipetted, as described and prepared above, onto the membranes—25 µL for each membrane. Antibody coated membranes were allowed to dry and were placed at the bottom of the antibody column.

Sample preparation. Standard proteins were first dissolved in water at a concentration of 1 mg/ml and then diluted with spray solvent (methanol/water 50:50 v:v, with 2% acetic acid) to the desired concentration. Experiments were performed on the same day that the protein samples were prepared.

Human plasma was separated from donor human blood from K2EDTA treated vials, and stored at -4° C. ATTR samples were stored at -20° C. and brought to room temperature prior to use. All plasma samples were diluted 1:10 with PBS buffer. Purchased antibodies were purified using the centrifugal filter to remove the azide from the store buffer. All plasma and buffer was warmed to room temperature prior to use.

Experimental Methods.

Direct Spray Ionization Using Paper and PE Substrate. Detection limits of standard protein samples were obtained by direct spray ionization from paper of PE substrate. The size of the pentangle shaped substrate was about 5 mm×8 mm (base×height). Standard protein samples were diluted with 50:50 (v:v) methanol-water with 2% acetic acid to different concentrations. A 20 µL sample was deposited to the rear of the substrate and wicked through the substrate to the tip by capillarity. The paper or PE substrate, which was cut to a sharp point, was positioned 5 mm away from atmospheric pressure inlet (302, FIG. 5) of the mass spectrometer (FIG. 5) and a high voltage of 5 kV was then applied to the spray substrate, inducing an electrospray at the tip of the substrate. The solvent evaporates from the charged droplets generated by the electrospray process, leaving gas phase ions of the analyte molecules, which can then be detected by a mass spectrometer.

Ionization Using Antibody Cartridge. As shown in the schematic of FIG. 5, diluted human plasma samples (1:10 dilution, 20 µL plasma diluted with 180 µL deionized water) were added to the antibody column. The sample wicked through the antibody column and subsequently onto the absorbent pad contained within the bottom part of the cartridge. As the sample passed through the antibody column (within 5 min), the target proteins were retained on the antibody column while the excess matrix was absorbed onto the waste pad.

The sample was then washed by applying 400 µL of deionized water to the antibody column; the deionized water also wicked through the column onto the absorbent pad. The target proteins were recovered from the antibody column and analyzed by sliding the column holder (as well as the antibody column) over and pushing the antibody column down so that the antibody column was in contact with the pentagon-shaped CNT-PE substrate rather than the waste pad. The cartridge was placed in front of the inlet to the mass spectrometer, and the extraction/spray solvent (typically 1:1 methanol:water with 2% acetic acid) was added to the top of the enrichment column/antibody column. The solvent wicked through the antibody column, recovering the proteins in the process, and onto the spray substrate passively.

For the detection of plasma TTR, 25 mM TECP-HCl was added to the spray solvent to perform the online reduction of the TTR posttranslational modifications. The reduction reaction was allowed to proceed on-cartridge for 5 minutes prior to ionization.

Ionization was induced directly from the paper substrate by applying a high voltage (5 kV typically) to the CNT-PE tip through a wire inserted from the side of the cartridge.

Mass Spectrometry, Data Collection, and Data Processing. The experiments of Example 2 as described further herein experiments were carried out with a Q Exactive Focus mass spectrometer (Thermo Fisher Scientific, San Jose, CA, USA). The instrument parameters were as follows: Positive ion mode in all experiments; Spray voltage typically 5 kV, spray voltage may vary in different cases to make the spray current at ~0.2 µA; Resolution 70,000; AGC target 1e6; Maximum injection time 100 ms; capillary temperature 320° C.; and S-lens RF level 60.0. In the detection of apolipoprotein, hemoglobin, and transthyretin from diluted human plasma sample, in-source CID was set at 25.0 eV, Microscans set at 1 for full MS scan and set at 5 for SIM scan, SIM scan window 7.0 Da for apolipoprotein and 1.2 Da for hemoglobin. The software MagTran was used to generate the deconvoluted MS spectra of human plasma transthyretin.

Example 2A. Reduction of Transthyretin (TTR) Posttranslational Modifications

Figure 17:
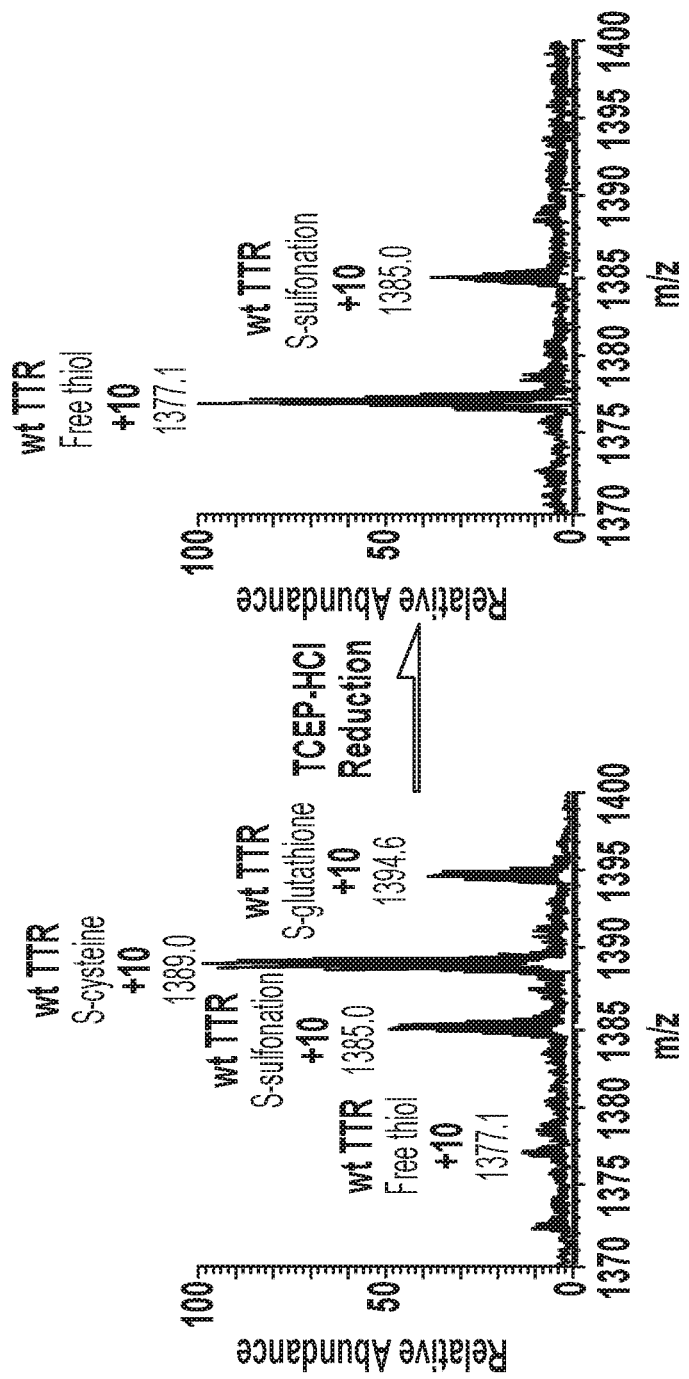
FIG. 17 provides mass spectra data illustrating the effect of TCEP-HCL reduction.

The reduction of TTR posttranslational modifications was performed during the protein extraction step. Tris(2-carboxyethyl)phosphine hydrochloride (TCEP-HCl) was spiked into the spray solvent (methanol:water 1:1 v:v, with 2% acetic acid) at a concentration 25 mM. As shown in FIG. 17, some high relative abundance posttranslational modifications, such as SCysteine and S-Glutathione were diminished after the TCEP-HCl reduction. The relative signal intensity of free thiol wild-type TTR increased significantly. However, posttranslational modifications S-Sulfonation still existed in the spectrum. Furthermore, increase in the concentration of TCEP-HCl (from 25 mM to 50 mM) or reduction time (from 5 min to 20 min) did not remove the S-Sulfonation TTR from the sample.

The reduction time was then optimized at 5 minutes with 25 mM TCEP-HCl in the spray solvent. The reduction greatly simplifies the data analysis and quantification of human plasma TTR, as well as the mutant. Additionally, TCEP-HCl reduction significantly reduces the posttranslational modifications of plasma TTR and enhances the MS response of free thiol wild-type TTR.

Example 2B—Protein Retention by the Spray Substrates

An 80 μL aliquot of a 3 μg/mL of cytochrome C from equine heart was dissolved in the spray solvent and passed through either the paper spray substrate or the CNT-PE spray substrate in a manner consistent with typical analysis. A 50 μL aliquot was recovered from each spray substrate, and the aliquot was spiked with 0.5 μg of an internal standard protein (cytochrome c from *Saccharomyces cerevisiae*). The recovery of two substrates can be compared using the following formula:

$$\frac{R_{CNT-PE}}{R_{paper}} = \frac{AUC_{A,CNT-PE}}{AUC_{A,paper}} \bigg/ \frac{AUC_{L,CNT-PE}}{AUC_{L,paper}} \quad (1)$$

Where $$\frac{R_{CNT-PE}}{R_{paper}}$$

is the relative recovery between the two substrates and AUCA and AUCL are the areas under the curve for the analyte and internal standard, respectively. In the case of cytochrome C, $$\frac{R_{CNT-PE}}{R_{paper}} \text{ was } 1.8 \pm 0.2 (N = 5),$$

indicating that the protein recovered from the CNT-PE substrate was approximately double the amount recovered from the paper substrate. This indicates that paper retained more target protein than CNT-PE. Because the limit of detection for cytochrome C was about 300× lower for the CNT-PE substrate compared to the paper, the lower retention by the CNT-PE is a relatively minor contributor compared to the improvement in ionization efficiency.

Example 2C—Recovery of Captured Protein

To determine the elution efficiency of the captured protein from the antibody column, antibody coated latex beads were incubated offline with 1.2 mL of a 10 μg/mL cytochrome c (equine heart) aqueous solution. The beads were then washed 3 times and divided into six equal aliquots. Three of them were coated to the membrane disc identically to the typical analysis. The other three were extracted offline using methanol:water 1:1 (v:v) with 2% acetic acid for 10 minutes while vortexing. For both samples, an internal standard (cytochrome C from *Saccharomyces cerevisiae*, 0.6 μg) was spiked into the elution/spray solvent.

The direct elution method used for the cartridge analysis was compared to offline recovery using equation 1 above.

$$\frac{R_{direct}}{R_{offline}} \text{ was found to be } 0.94 (N = 3),$$

indicating that extended offline extraction did not elute anymore protein than the direct elution method used in the protein cartridge.

In a second experiment, the latex bead coated membranes were removed from the cartridge after analysis and subjected to offline extraction as described above. No protein was detectable in the offline extraction. This indicates that virtually all of the protein was eluted from the beads during the direct elution.

Figure 19A:
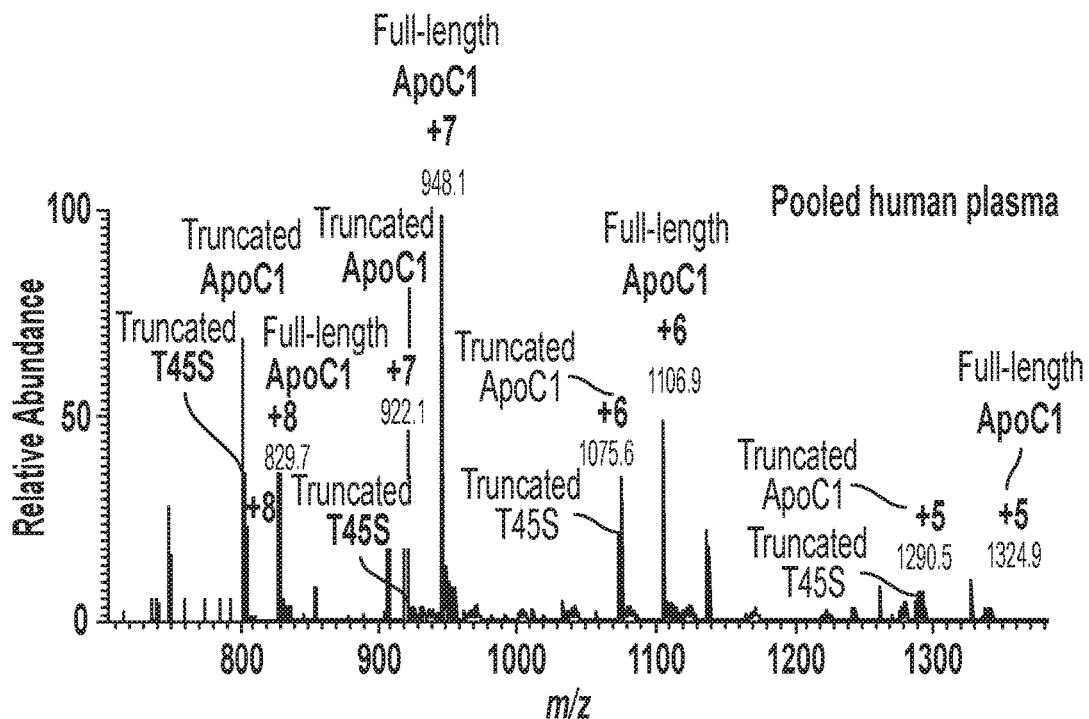
FIG. 19A is related to Example 3 and provides a full MS spectrum obtained from the pooled human plasma sample showing ApoC1 full-length, truncated, and truncated T45S variant.
Figure 19B:
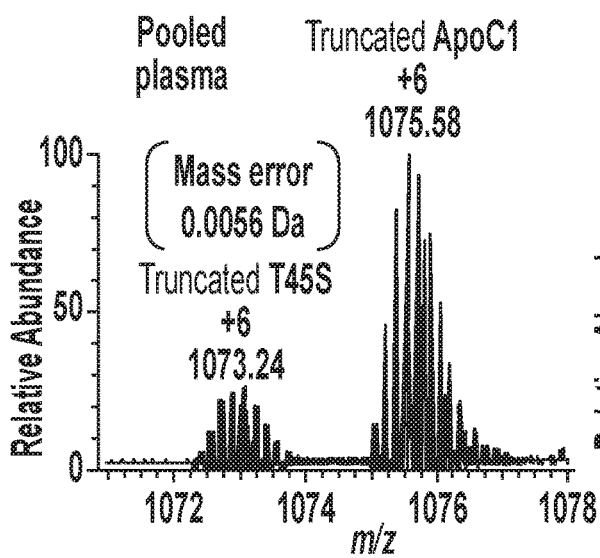
FIG. 19B is related to Example 3 and shows a narrower MS scan range showing the truncated ApoC1+6 ions and truncated T45S variant +6 ions obtained from pooled human plasma.
Figure 19C:
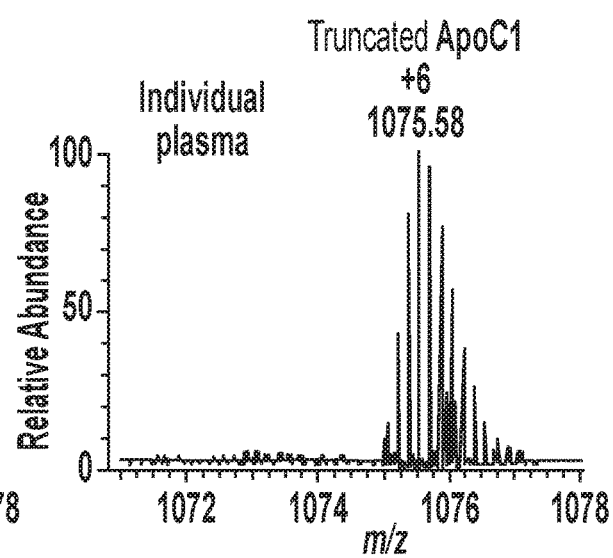
FIG. 19C is related to Example 3 and shows a narrower MS scan range showing the truncated ApoC1+6 ions obtained from individual donated plasma.

Example 3—Identification of T45S Variant of Apolipoprotein c1 (a Polymorphism Associated with Body Mass Index and Obesity Apolipoprotein C1 (ApoC1) T45S variant is a naturally occurring amino acid polymorphism that has been associated with elevated body mass index and diabetes. As shown in FIG. 19A, three ApoC1 species were identified in the mass spectrometry (MS) spectrum obtained from a pooled human plasma sample, including full-length ApoC1 (6.6 kDa), truncated ApoC1 (minus amino-terminal Thr-Pro, 6.4 kDa), and truncated T45S variant (Δm=−14.03 Da). Detection of the T45S variant in the pooled plasma sample indicated that some of the plasma came from individuals with the ApoC1 S45 allele (FIG. 19B). The protein cartridge was also used to analyze plasma from a single donor; the mass spectrum indicates that the individual donor did not have this allele (FIG. 19C). In comparison with calculated accurate masses, mass error for detected T45S variant was 0.0056 Da. These results indicate the method has good potential for rapid detection of the ApoC1 T45S variant.

Figure 20A:
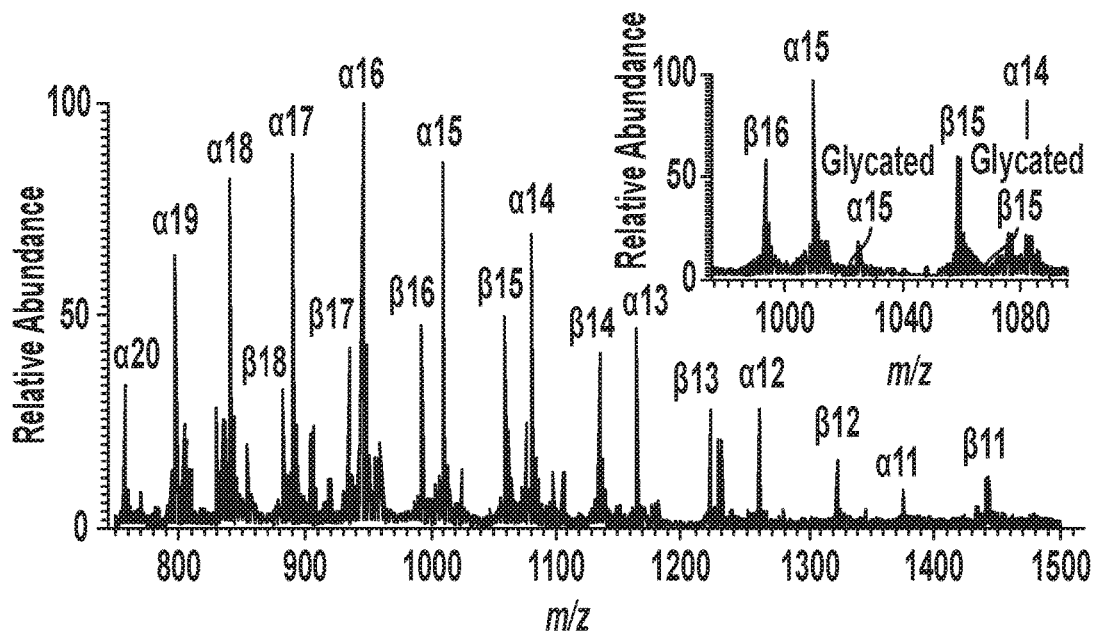
FIG. 20A is related to Example 4 and shows an antibody cartridge analysis of human plasma hemoglobin where a full MS spectrum shows the Hb α-/β-chain ions with charge state from +11 to +20.
Figure 20B:
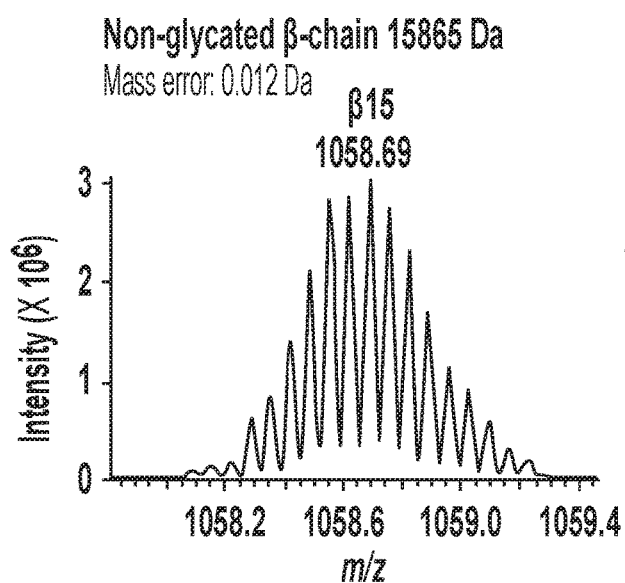
FIG. 20B is related to Example 4 and shows an antibody cartridge analysis of human plasma hemoglobin where a SIM spectra (m/z scan window 1.2 Da) shows the relative intensities of non-glycated Hb.
Figure 20C:
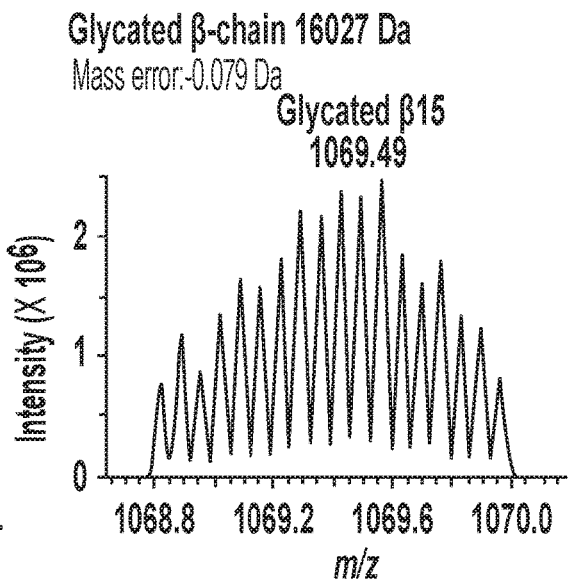
FIG. 20C is related to Example 4 and shows an antibody cartridge analysis of human plasma hemoglobin where a SIM spectra (m/z scan window 1.2 Da) shows the relative intensities of glycated Hb.

Example 4—Relative Quantitation of Hemoglobin (Hb) A1C, a Marker of Diabetes Glycated hemoglobin is a stable minor Hb variant formed in vivo by the nonenzymatic, covalent attachment of glucose. Relative quantitation of a particular Hb fraction, HbA1c, has been used as a marker of glycemia control in diabetes for decades. As shown in FIGS. 20A-C, several hemoglobin species were identified using the protein detection cartridge, such as nonglycated α-/β-chains (FIG. 20A) and glycated α-/β-chains (FIG. 20A insert spectrum). The Hb and glycated Hb were monitored using single ion monitoring (SIM) of the +15 charge state as shown in FIGS. 20B and 20C. The mass error for the detected nonglycated Hb β-chain and glycated Hb β-chain were 0.012 Da and −0.079 Da, respectively. The relative intensity of glycated Hb was ~7% compared to unglycated Hb, which is similar to the expected proportion. The results indicate the method has potential for relative quantitation of Hb and HbA1c.

Example 5—Identification of Sequence Variants of Transthyretin (TTR), (Markers of Transthyretin-Related Hereditary Amyloidosis)

Transthyretin (TTR) is a 55 kDa homotetramer protein that transports thyroxine and retinol in blood and cerebrospinal fluid. Misfolding and aggregation of wild-type (wt)

and mutant transthyretin protein (TTR) is the cause of transthyretin amyloidosis (ATTR), a severe and fatal disease characterized by abnormal deposits of TTR amyloids. Mass spectrometry is used to screen for ATTR. The antibody cartridge was successfully used to detect wt TTR as well as various TTR mutants from human plasma samples.

Figure 21A:
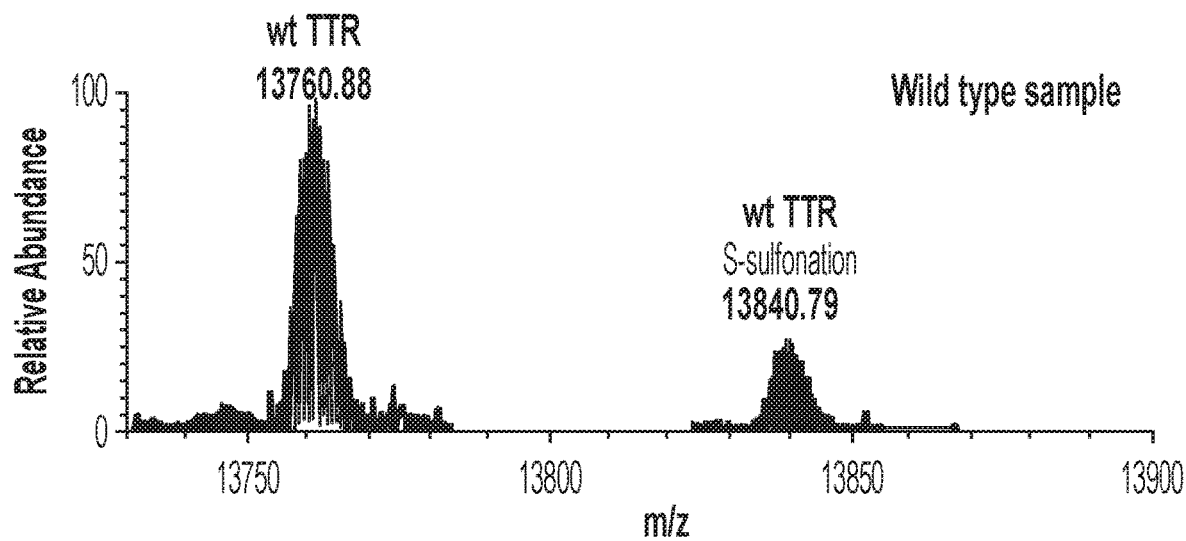
FIG. 21A is related to Example 5 and show a charge-state deconvoluted MS spectra obtained by antibody cartridge analysis of human plasma from a wild-type (wt) sample.
Figure 21B:
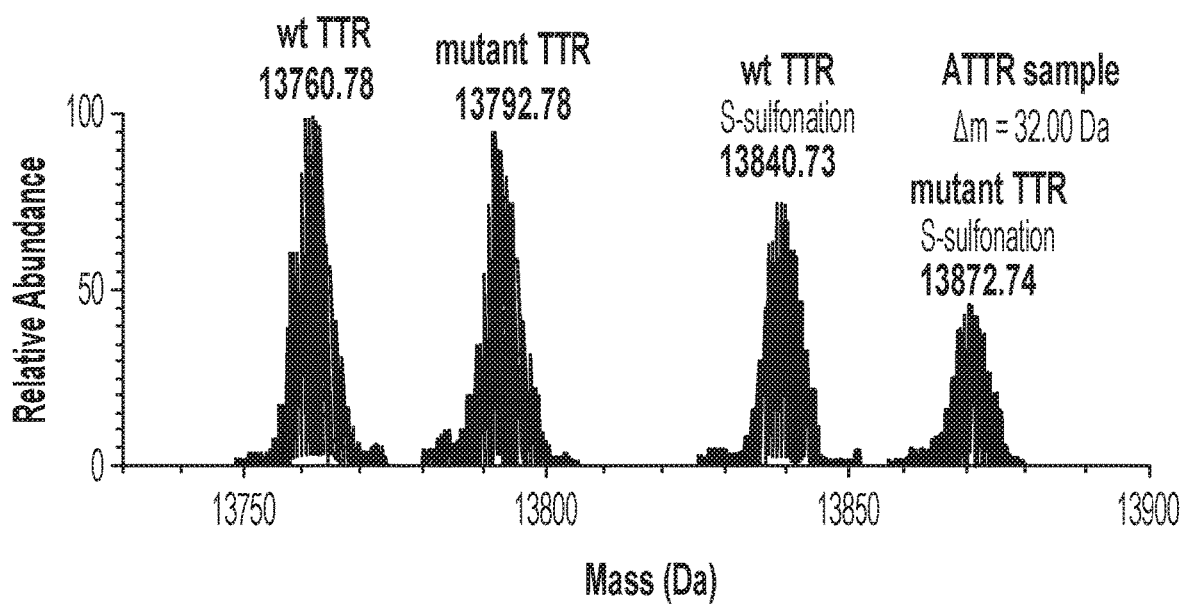
FIG. 21B is related to Example 5 and show a charge-state deconvoluted MS spectra obtained by antibody cartridge analysis of human plasma from a ATTR plasma sample.

FIG. 17 shows the mass spectrum obtained for the +10 charge state of wt TTR. The unmodified TTR was a relatively minor component; the cysteine, glutathione, and sulfonate PTMs were all more intense. To reduce the complexity of the mass spectrum, the reducing agent Tris(2-carboxyethyl)phosphine hydrochloride (TCEP-HCl) was spiked into the spray solvent. This procedure, performed on-cartridge in the extraction/spray solvent without a separate step, succeeded in eliminating the S-cysteine and S-glutathione modifications (FIG. 17), although the S-sulfonation remained. Four different TTR mutants in six ATTR clinical samples were clearly identified and differentiated from wt TTR. FIGS. 21A and 21B show the charge-state deconvoluted mass spectra obtained from a wt sample (FIG. 21A) and a representative ATTR sample (FIG. 21B). The spectrum from the ATTR sample (FIG. 21B) indicates the patient is heterozygous for wild type TTR and a TTR variant with a Δm of 32.00 Da. This mass shift is consistent with substitution of valine-30 for methionine, the most common mutation found in TTR associated neuropathy.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A protein detection cartridge comprising:
a lid including an opening;
a base coupled to the lid and including a recess;
a column holder removably positioned in the opening, the column holder including an aperture;
an antibody column received within the aperture and moveable within the aperture;
a waste pad removably positioned in the recess of the base;
a spray tip holder positioned in the base, the spray tip holder including a recess; and
an enzyme immobilized membrane positioned in the recess of the spray tip holder;
wherein the column holder is movable between a first position where the antibody column is positioned over the waste pad and a second position where the antibody column is positioned over the enzyme immobilized membrane; and
wherein, with the column holder in the second position, the antibody column is configured to be pushed downwardly into the recess of the spray tip holder and into contact with the enzyme immobilized membrane.

2. The protein detection cartridge of claim 1, wherein the column holder is movable between the first position and the second position along a groove between the lid and the base.

3. The protein detection cartridge of claim 1, wherein the antibody column includes an antibody coated membrane configured to retain target proteins.

4. The protein detection cartridge of claim 1, further comprising a spray substrate coupled to the spray tip holder with the enzyme immobilized membrane positioned over the spray substrate, the spray substrate configured to provide a sample to a mass spectrometer, the spray substrate is coated with carbon nanotube treated porous polyethylene.

5. The protein detection cartridge of claim 1, wherein the cartridge is coupled to an electrical power source.

6. A protein detection cartridge comprising:
a lid including an opening;
a base coupled to the lid and including a recess;
a column holder removably positioned in the opening; the column holder including an aperture;
an antibody column received within the aperture and moveable within the aperture;
a waste pad removably positioned in the recess of the base;
a spray tip holder positioned in the base, the spray tip holder including a recess;
an enzyme immobilized membrane positioned in the recess of the spray tip holder; and
a spray substrate coupled to the spray tip holder such that the enzyme immobilized membrane is positioned over the spray substrate;
wherein the column holder is slidable within the cartridge between a first position and a second position; and
wherein, in the first position, the antibody column is positioned over the waste pad and, in the second position, the antibody column is positioned over the enzyme immobilized membrane and the spray substrate; and
wherein, in the second position, the antibody column is moveable, within the aperture, into the recess of the spray tip holder and into contact with the enzyme immobilized membrane.

7. The protein detection cartridge of claim 6, wherein the spray substrate is coated with carbon nanotube treated porous polyethylene.

8. The protein detection cartridge of claim 6, wherein the antibody column includes an antibody coated membrane to retain target proteins of a sample when the antibody column is in the first position.

9. The protein detection cartridge of claim 6, wherein, in the second position, the enzyme immobilized membrane digests target proteins into peptides.

10. The protein detection cartridge of claim 6, wherein the column holder is movable between the first position and the second position along a groove between the lid and the base.

11. The protein detection cartridge of claim 6, wherein the spray substrate is coupled to a mass spectrometer.

12. The protein detection cartridge of claim 6, wherein the cartridge is coupled to an electrical power source.

13. A method of using a protein detection cartridge for mass spectrometry comprising:
setting a column holder of the protein detection cartridge in a first position, wherein the column holder includes an aperture movably receiving an antibody column therein;
inserting a plasma sample into the antibody column of the protein detection cartridge, the plasma sample comprising proteins;
with the column holder in the first position, inserting a wash buffer into the antibody column;
sliding the column holder to a second position, wherein the antibody column is above an enzyme immobilized membrane positioned in a recess of the protein detection cartridge;
pushing the antibody column into the recess and into contact with the enzyme immobilized membrane; and inserting an elution buffer into the antibody column to cause the proteins in the antibody column to exit onto the enzyme immobilized membrane, the enzyme immobilized membrane digesting the proteins to form a peptide.

14. The method of claim 13, wherein the antibody column includes an antibody coated membrane to retain target proteins of a sample when the antibody column is in the first position.

15. The method of claim 13, further including applying the peptide onto a spray substrate.

16. The method of claim 15, wherein the spray substrate is coated with carbon nanotube treated porous polyethylene.

17. The method of claim 16, wherein the spray substrate is coupled to a mass spectrometer.

18. The method of claim 17, wherein the cartridge is coupled to an electrical power source.

19. The protein detection cartridge of claim 1, wherein the spray tip holder is integral with or removable from the base.

20. The protein detection cartridge of claim 6, wherein the spray tip holder is integral with or removable from the base.

* * * * *